US009469856B2

(12) United States Patent
Dou et al.

(10) Patent No.: US 9,469,856 B2
(45) Date of Patent: *Oct. 18, 2016

(54) INDUCIBLE EUKARYOTIC EXPRESSION SYSTEM

(71) Applicant: REGENERON PHARMACEUTICALS, INC., Tarrytown, NY (US)

(72) Inventors: Changlin Dou, Yantai (CN); Gang Chen, Yorktown Heights, NY (US); James P. Fandl, LaGrangeville, NY (US)

(73) Assignee: REGENERON PHARMACEUTICALS, INC., Tarrytown, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/182,863

(22) Filed: Feb. 18, 2014

(65) Prior Publication Data

US 2014/0315249 A1    Oct. 23, 2014

Related U.S. Application Data

(63) Continuation of application No. 12/323,161, filed on Nov. 25, 2008, now Pat. No. 8,673,589, which is a continuation-in-part of application No. 11/332,431, filed on Jan. 13, 2006, now Pat. No. 7,514,545, and a (Continued)

(51) Int. Cl.
  *C12N 15/63* (2006.01)
  *C12N 15/85* (2006.01)
  *C07K 16/00* (2006.01)

(52) U.S. Cl.
  CPC ............ *C12N 15/635* (2013.01); *C07K 16/00* (2013.01); *C12N 15/63* (2013.01); *C12N 15/85* (2013.01);

(Continued)

(58) Field of Classification Search
  None
  See application file for complete search history.

(56) References Cited

U.S. PATENT DOCUMENTS 4,833,080 A    5/1989    Brent et al.
5,096,815 A    3/1992    Ladner et al.

(Continued)

FOREIGN PATENT DOCUMENTS

AU    1999054262 A    3/2000
WO    9007862 A2    7/1990

(Continued)

OTHER PUBLICATIONS

Guo et al., Protein tolerance to random amino acid change, 2004, Proc. Natl. Acad. Sci. USA 101: 9205-9210.*

(Continued)

*Primary Examiner* — Alexander Kim
(74) *Attorney, Agent, or Firm* — Regeneron Pharmaceuticals, Inc.; Mary C. Johnson

(57) ABSTRACT

Compositions and methods for the inducible expression of genes in eukaryotic cells are provided. Expression of a nucleotide sequence of interest encoding a protein of interest is controlled by a regulatory fusion protein that consists of a transcription blocking domain and a ligand-binding domain. When a cognate ligand for the ligand-binding domain is present, transcription of the nucleotide sequence of interest is blocked. Upon removal of the cognate ligand, the nucleotide sequence of interest is transcribed. The method is useful for large scale bioreactor production of a desired protein of interest in eukaryotic cells.

20 Claims, 14 Drawing Sheets

Related U.S. Application Data continuation-in-part of application No. 10/447,243, filed on May 28, 2003, now Pat. No. 7,455,988, said application No. 11/332,431 is a continuation of application No. 10/447,243, filed on May 28, 2003, now Pat. No. 7,455,988.

(60) Provisional application No. 60/384,004, filed on May 29, 2002.

(52) U.S. Cl.
CPC ....... A01K 2217/05 (2013.01); C07K 2319/00 (2013.01); C12N 2830/00 (2013.01); C12N 2830/15 (2013.01); C12N 2830/42 (2013.01); C12N 2840/20 (2013.01)

(56) References Cited

U.S. PATENT DOCUMENTS

| | | | |
|---|---|---|---|
| 5,198,346 | A | 3/1993 | Ladner et al. |
| 5,599,904 | A | 2/1997 | Evans et al. |
| 5,650,298 | A | 7/1997 | Bujard et al. |
| 5,739,018 | A | 4/1998 | Miyanohara et al. |
| 5,756,448 | A | 5/1998 | Moore et al. |
| 5,972,650 | A | 10/1999 | Yao |
| 6,117,680 | A | 9/2000 | Natesan et al. |
| 6,183,965 | B1 | 2/2001 | Verdine et al. |
| 6,271,348 | B1 | 8/2001 | Bujard et al. |
| 6,432,705 | B1 | 8/2002 | Yee et al. |
| 7,112,715 | B2 | 9/2006 | Chambon et al. |
| 7,153,685 | B2 | 12/2006 | Mao et al. |
| 8,673,589 | B2 | 3/2014 | Chen et al. |
| 2002/0115629 | A1 | 8/2002 | Ramachandra |
| 2003/0186841 | A1 | 10/2003 | Barbas et al. |
| 2004/0102367 | A1 | 5/2004 | Gage et al. |

FOREIGN PATENT DOCUMENTS

| | | |
|---|---|---|
| WO | 9429442 A2 | 12/1994 |
| WO | 9601313 A1 | 1/1996 |
| WO | 9910510 A2 | 3/1999 |
| WO | 0012741 A2 | 3/2000 |
| WO | 0130843 A | 5/2001 |

OTHER PUBLICATIONS

Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Hammill et al., The gel microdrop secretion assay: Identification of a low productivity subpopulation arising during the production of human antibody in CHO cells., Cytotechnology (2000), vol. 34, pp. 27-37.*
Borgna, et al, "High-Affinity Binding to the Estrogen Receptor of [3H] 4-Hydroxytamoxifen, an Active Antiestrogen Metabolite", Mol. Cell. Endocrin., 20, pp. 71-85, 1980.
Deuschle et al, "Tetracycline-reversible silencing of eukaryotic promoters", Mol. Cell. Biology, 15(4), pp. 1907-1914, 1995.
Feil, et al, "Regulation of Cre Recobminase Activity by Mutated Estrogen Receptor Ligand-Binding Domains, Biochem", Biophys. Res. Commun., 237, pp. 752-757, 1997.
Golemis, et al, "Fused Protein Domains Inhibit DNA Binding LexA", Mol. & Cell. Biol. ,1217, pp. 3006-3014, 1992.
Gossen, et al, "Tight control of gene expression in mammalian cells by tetracycline-responsive promoters", PNAS, vol. 89, pp. 5547-5551, 1992.
Guo, et al, "Protein tolerance to random amino acid change", Proc. Natl. Acad. Sci. USA, 101, pp. 9205-9210, 2004.
Hammill, et al, "The gel microdrop secretion assay: Identification of a low productivity subpopulation arising during the production of human antibody in CHO cells", Cytotechnology, vol. 34, pp. 27-37, 2000.
Hill, et al, "Functional Analysis of conserved Histidines in ADP-Glucose Pyrophosphorylase from *Escherichia coli*", Biochem. Biophys. Res. Comm., 244, pp. 573-577, 1998.
Iida, et al, "Inducible gene expression by retrovirus-mediated transfer of a modified tetracycline-regulated system", J. Virology, 70(9), pp. 6054-6059, 1996.
Knight, et al, "The Arc and Mnt Repressors: A new Class of Sequence-Specific DNA-Binding Protein", J. Biol. Chem., 2641(7), pp. 3639-3642, 1989.
Kumar, et al, "The structure of the nuclear hormone receptors", Steroids, 64, pp. 310-319, 1999.
Lazar, et al, "Transforming growth factor alpha: mutation of aspartic acid 47 and leucine 48 results in different biological activities", Mol. Cell. Biol., 8(3), pp. 1247-1252, 1988.
Lee, et al, "A chimeric thyroid hormone receptor constitutively bound to DNA requires retinoid X receptor for hormone-dependent transcriptional activation in yeast", Mol. Endocrin, 8, pp. 1245-1252, 1994.
Littlewood, et al, "A modified oestrogen receptor ligand-binding domain as an improved switch for the regulation of heterologous proteins" Nucleic Acids Res., 23(10), pp. 1686-1690, 1995.
Ma, et al, "Suppression of gene expression by tethering KRAB domain to promoter or ER target genes", Journal of Steroid Biochemistry and Molecular Biology, vol. 69, pp. 155-163, 1999.
Mattioni, et al, "Regulation of protein activities by fusion to steroid binding domains", Methods in Cell Biology, 43, pp. 335-352 (XP002097158), 1994.
No, et al, "Ecdysone-inducible gene expression in mammalian cells and transgenic mice", Proc. Natl. Acad. Sci. USA, 93(8), pp. 3346-3351, 1996.
Richards, "Protein stability: still an unsolved problem", Cell Mol. Life Sci., 53, pp. 790-802, 1997.
Robinson, et al, "Optimizing the stability of single-chain proteins by linker length and composition mutagenesis", Proc. Natl. Acad. Sci. USA, 95, pp. 5929-5934, 1998.
Smith, et al, "Dual regulation of open-complex formation and promoter clearance by Arc explains a novel repressor to activator switch", PNAS, vol. 93, pp. 8868-8872, 1996.
Sun, et al, "Development of a tetracycline controlled gene expression system in the parasite protozoan Giardia lamblia", Molecular and Biochemical Parasitology, vol. 105, pp. 51-60, 2000.
Wang, et al, "Positive and negative regulation of gene expression in eukaryotic cells with an inducible transcriptional regulator", Gene Therapy, vol. 4, pp. 432-441, 1997.
Wacey, et al, "Disentangling the perturbational effects of amino acid substitutions in the DNA-binding domain of p53", Hum Genet, Vo. 104, pp. 15-22, 1999.
Blair, R.M. et al., The Estrogen Receptor Relative Binding Affinities of 188 Natural and Xenochemicals: Structural Diversity of Ligands. (2000), Toxicological Sciences, 54:138-153.
Eilers, M. et al. Chimaeras of Myc oncoprotein and streroid receptors cause hormone-dependent transformation of cells. (1989) Nature, 340:66-68.
Louvion, J.-F. et al. Fusion of GAL4-VP16 to a steroid-binding domain provides a tool for gratuitous induction of galactose-responsive genes in yeast (1993) Gene, 131:129-134.

* cited by examiner

FIG. 6.

```
                    arcO                              arcO
TATAAGCAGAGCTCATGATAGAATCACTCTACTATTCATGATAGAAGCACTCTACTAT
ATATTCGTCTCGAGTACTATCTTAGTGAGATGATAAGTACTATCTTCGTGAGATGATA
```

INDUCIBLE EUKARYOTIC EXPRESSION SYSTEM

STATEMENT OF RELATED PATENT APPLICATIONS

This application is a continuation of U.S. patent application Ser. No. 12/323,161, filed 25 Nov. 2008, now allowed, which is a continuation-in-part of U.S. patent application Ser. No. 11/332,431, filed 13 Jan. 2006, now U.S. Pat. No. 7,514,545, which is a continuation of U.S. patent application Ser. No. 10/447,243, filed 28 May, 2003, now U.S. Pat. No. 7,455,988; and U.S. patent application Ser. No. 12/323,161, filed 25 Nov. 2008, now allowed, is also a continuation-in-part of U.S. patent application Ser. No. 10/447,243, filed 28 May, 2003, now U.S. Pat. No. 7,455,988, which claims the benefit under 35 USC §119(e) of U.S. Provisional Application No. 60/384,004, filed 29 May 2002; all of which are herein incorporated by reference.

SEQUENCE LISTING

This application incorporates by reference the Sequence Listing submitted in Computer Readable Form as file 85000N2_ST25.txt created on Feb. 14, 2014 (12,780 bytes).

FIELD OF THE INVENTION

The present invention relates to methods for the inducible expression of genes in eukaryotic cells, nucleotide sequences and proteins comprising regulatory fusion proteins, cells capable of inducible gene expression, and methods for protein expression in bioreactors.

BACKGROUND

Various methods for controlled expression of a recombinant nucleotide sequence of interest in a cell are known to the art. For example, No et al. (1996) Proc. Natl. Acad. Sci. USA 93:3346-3351, describe an inducible gene expression system utilizing a chimeric transactivator consisting of the ecdysone nuclear receptor fused to the VP16 transactivation domain. In the presence of inducer, this chimeric transactivator binds to recognition sequences upstream from a promoter and stimulates transcription of a nucleotide sequence of interest. In the absence of inducer, expression of the nucleotide sequence of interest is reduced and dependent on the basal level of transcription from the nucleotide sequence of interest promoter. Gossen et al. (1992) Proc. Natl. Acad. Sci. USA 89:5547-5551, describe a system for regulating expression of a nucleotide sequence of interest based on a chimeric protein, tTA, consisting of the TetR repressor protein fused with the VP16 transactivation domain. Similar to the ecdysone system, the DNA sequences specifying the TetR DNA binding site are inserted upstream of the gene promoter such that binding of the TetR-VP16 fusion protein stimulates transcription from the promoter and expression of the nucleotide sequence of interest. Other systems targeted to specific DNA binding sites proximal to a minimal promoter for targeted regulation of transcription utilizing the VP16 transactivation domain have also been developed, including GAL4-VP16 (Sadowski et al. (1988) Nature 335:563-564), LexA-VP16 (Brent et al. (1985) ET 712521864 US Cell 40:729-736), and LacI-VP16 (Labow et al. (1990) Mol. Cell. Biol. 10:3342-3356). Other TetR-based systems are described in Deuschle et al. (1995) Mol. Cell. Biol. 15:1907-1914 and Yao et al. (1998) Hum. Gene Ther. 13:1939-1950.

Problems resulting from leaky expression related to the use of a minimal promoter have led to systems using fusions of the steroid-binding domains of the glucocorticoid or estrogen nuclear receptors (see, for example, Mattioni et al. (1994) Methods Cell Biol. 43:335-352; Louvion et al. (1993) Gene 131:129-134; Iida et al. (1996) J. Virol. 70: 6054-6059.

BRIEF SUMMARY

A tightly regulated inducible gene expression system is provided that is suitable for large-scale production of a recombinant molecule of interest in a eukaryotic cell. The components of the system include a fusion protein having a transcription blocking domain and a ligand-binding domain; an operator that binds the transcription blocking domain of the fusion protein to inhibit transcription of a nucleotide sequence; and a promoter that is under the control of the operator. When expression of the nucleotide sequence of interest is desired to be inhibited, the system includes a ligand that is capable of binding the ligand-binding domain of the fusion protein, such that the fusion protein is stabilized. When it is desired that the nucleotide sequence of interest be expressed, the ligand is removed, which results in destabilization and degradation of the fusion protein. Accordingly, in the absence of the cognate ligand, the fusion protein is removed from the operator, and operator-inhibition of the promoter controlling expression of the nucleotide sequence of interest is removed, thereby allowing the nucleotide sequence of interest to be expressed.

Methods and compositions are provided that help to control the timing of induction of a protein of interest in a cell culture. The methods and compositions include any suitable combination or application of the embodiments disclosed herein. One suitable application for the methods and compositions includes expression of a protein of interest in a large scale (i.e., hundreds to thousands of liters in capacity) bioreactor.

In one aspect, a method of inducing expression of a nucleotide sequence of interest in a eukaryotic cell is provided, comprising (a) providing a eukaryotic cell comprising (i) a nucleotide sequence encoding a regulatory fusion protein (RPR), wherein the fusion protein consists of (1) a transcription blocking domain capable of inhibiting expression of the nucleotide sequence of interest, and (2) a ligand-binding domain; (ii) a promoter operably linked to the nucleotide sequence of interest and controlled by an operator that binds the fusion protein; and (iii) an operator capable of binding the transcription blocking domain and blocking transcription from the adjacent promoter; (b) growing the cell of step (a) to a desired density in the presence of a ligand that binds the ligand-binding domain of the fusion protein, wherein expression of the nucleotide sequence of interest is inhibited; and (c) removing the ligand from the presence of the cell, wherein expression of the nucleotide sequence of interest is induced.

The transcription blocking domain is a protein capable of binding DNA and blocking transcription from an adjacent promoter. In more specific embodiment, the transcription blocking domain may be derived from a bacterial, bacteriophage, eukaryotic, or yeast repressor protein. In more specific embodiments, the transcription blocking domain is derived from a bacterial or bacteriophage repressor protein. In even more specific embodiments, the transcription blocking domain is derived from a repressor protein selected from the group consisting of TetR, LexA, LacI, TrpR, Arc; and LambdaC1. In another embodiment, the transcription blocking domain is derived from a eukaryotic repressor protein. In an even more specific embodiment, the repressor domain is derived from GAL4.

In another specific embodiment of the method of the invention, the transcription blocking domain is a mutated restriction enzyme capable of binding but not cleaving DNA, and the operator is a recognition site for the restriction enzyme. In a more specific embodiment, the transcription blocking domain is a mutated NotI.

In specific embodiments, the ligand-binding domain is derived from a steroid, thyroid, or retinoid receptor. In more specific embodiments, the ligand-binding domain is derived from an estrogen receptor, and the cognate ligand is an estrogen. In an even more specific embodiment, the estrogen receptor contains one or more mutations, for example, the T2 mutations, and the cognate ligand is tamoxifen.

A variety of eukaryotic cells may be used in the method of the invention, including without limitation, a yeast cell, such as Pichia pastoris, or a mammalian cell, such as a COS, CHO, 293, BHK, cell lines transfected with adenovirus genes, for example, AD5 E1, including but not limited to an immortalized human retinal cell transfected with an adenovirus gene, for example, a PER.C6™ cell, or an NSO cell.

The instant invention may be broadly used in the transcription of a nucleotide sequence of interest, and the product of interest may be the transcription product, e.g., an mRNA or catalytically active RNA, or a downstream product resulting from the transcribed nucleotide sequence of interest, for example, a protein or protein fragment, including without limitation, a hormone, a receptor or receptor fragment, an antibody or antibody fragment, a biologically active peptide or protein, an enzyme, a repressor protein, or a DNA binding protein.

In another aspect, a method for expressing a protein of interest in a cell in a bioreactor is provided, comprising inducing expression of the protein of interest by reducing concentration of an inhibitor that inhibits expression of the protein of interest. In one embodiment, reducing concentration is achieved by removing, or diluting, an inhibitor that prevents expression of the protein of interest.

In one embodiment, the protein of interest is an antibody.

In one embodiment, the inhibitor that prevents expression of the protein of interest is a ligand that binds a ligand-binding domain of a regulatory fusion protein of the invention. In a specific embodiment, the regulatory fusion protein consists essentially of a first domain and a second domain, wherein the first domain comprises a ligand-binding domain of a human estrogen receptor, and the second domain comprises an Arc repressor, and the ligand is selected from estrogen and tamoxifen.

In another embodiment, the method comprises (a) providing a eukaryotic cell comprising (i) a promoter operably linked to the nucleotide sequence of interest; (ii) a bacterial or bacteriophage operator located downstream of the promoter; and (iii) a nucleotide sequence encoding a regulatory fusion protein, wherein the regulatory fusion protein consists of (1) a bacterial or bacteriophage transcription blocking domain, wherein the bacterial or bacteriophage transcription blocking domain binds directly to the bacterial or bacteriophage operator, and (2) a ligand-binding domain of a nuclear hormone receptor, wherein the bacterial or bacteriophage transcription blocking domain binds the bacterial or bacteriophage operator in the presence of ligand binding the ligand-binding domain of the estrogen receptor and blocks expression of the nucleotide sequence of interest; (b) growing the cell of step (a) to a desired density in the presence of ligand; and (c) reducing concentration of the ligand to a non-inhibitory or substantially non-inhibitory concentration, such that the expression of the nucleotide sequence of interest is induced.

In a specific embodiment, the bacterial or bacteriophage operator is selected from a tet operator and an Arc operator. In another specific embodiment, the nuclear hormone receptor is the estrogen receptor.

In another specific embodiment, the bacterial or bacteriophage transcription blocking domain has either (i) amino acids M1 to S207 of SEQ ID NO:7, or (ii) an Arc repressor dimer comprising Arc monomers connected by a linker, and a bacterial or bacteriophage operator is selected from a tet operator and an Arc operator.

In another specific embodiment, the ligand-binding domain is a modified ligand-binding domain of a human estrogen receptor. In a specific embodiment, the ligand-binding domain comprises the amino acid sequence of N304 to V595 of SEQ ID NO:8. In another specific embodiment, the modifications are one or more of G400V, M543A, and L544A. In another specific embodiment, the ligand-binding domain consists of N304 to V595 of SEQ ID NO:8. In a specific embodiment, the ligand is selected from the group consisting of tamoxifen and estrogen and a combination thereof.

In another embodiment, the method is practiced in a bioreactor process, wherein the eukaryotic cell is contained in a cell culture employed in a seed train to ultimately seed a 3,000 liter bioreactor followed by a 10,000 liter bioreactor, and reducing the concentration of the ligand occurs in the 3,000 liter and/or 10,000 liter bioreactor. In a specific embodiment, the seed train for the bioreactor is as shown in FIG. 11A.

In one embodiment, the ultimate bioreactor is a 10,000 liter bioreactor, wherein the 10,000 liter bioreactor is seeded from a (penultimate) 3,000 liter bioreactor, the 3,000 liter bioreactor is seeded from a 500 liter bioreactor, which is seeded from a 50 liter bioreactor, which is seeded from a 10 liter bioreactor.

In another specific embodiment, the 10 liter bioreactor comprises a sufficient concentration of inhibitor to maintain inhibition of expression of the protein of interest at all stages other than the 10,000 liter stage. In another embodiment, the 10 liter bioreactor comprises a sufficient concentration of inhibitor to maintain inhibition of expression of the protein of interest through the 500 liter stage, but does not substantially inhibit expression in the 3,000 liter bioreactor stage, allowing for a pre-induction period prior to the 10,000 liter bioreactor stage.

In a specific embodiment, the concentration of ligand is sufficient to allow a pre-induction stage at the 3,000 liter bioreactor stage such that maximum titer is achieved in the 10,000 liter bioreactor at about 2-10 days, more preferably at about 2 to 6 days following seeding of the 10,000 liter bioreactor. In specific embodiments, pre-incubation periods in the 3,000 liter bioreactor are 1, 2, 3, 4, 5, 6, or 7 days, and in a specific embodiment about 3 to 5 days. In a particular embodiment, pre-induction in the 3,000 liter bioreactor is about 4 days.

In another aspect, a method for expressing a protein of interest in a eukaryotic cell is provided, comprising: (a) incubating cells in a cell culture in the presence of a ligand, wherein the cells contain a regulatory fusion protein that binds the ligand, wherein the ligand prevents expression of a protein of interest in the cells, wherein the cells are incubated for an amount of time sufficient for the cells to reach a desired cell density, (b) diluting the cell culture such that the ligand no longer prevents expression of the protein of interest, (c) allowing the cells to express the protein of interest; and (d) recovering the protein of interest.

In another aspect, a method for expressing a protein of interest in a cell in culture in a bioreactor process culminating in a culture of at least 10 liters is provided, comprising: (a) incubating cells in media in the presence of a ligand, wherein the cells contain a regulatory fusion protein that binds the ligand, wherein the ligand prevents expression of a protein of interest in the cells, wherein the cells are incubated for an amount of time sufficient for the cells to reach a desired cell density, and (b) diluting the cells in media that do not contain the ligand, such that the ligand no longer prevents expression of the protein of interest, (c) allowing the cells to express the protein of interest; and (d) recovering the protein of interest.

In one embodiment, the culture is at least 50 liters. In another embodiment, at least 100 liters. In another embodiment, at least 500 liters. In another embodiment, at least 3,000 liters. In another embodiment, about 10,000 liters.

In one embodiment, the cells in media in the presence of the ligand are not isolated or separated from the media upon dilution in media that does not contain the ligand.

Another aspect, a method is provided for expressing a protein of interest in a bioreactor process, wherein the process comprises growing a eukaryotic cell comprising a regulatory fusion protein as described herein and a gene for a protein of interest whose transcription is controlled by the regulatory fusion protein, and enhancing expression of the protein of interest by removing, depleting, or diluting the concentration in culture of a ligand that binds the regulatory fusion protein.

In one embodiment, expression is enhanced no more than about 5% to about 40% in a day; no more than about 10% to about 60% in about two days; no more than about 30% to about 80% in about three days; no more than about 40% to about 90% in four days; or less than about 90% in about 5 days.

In specific embodiments, expression is enhanced: no more than about 5%, 10%, 15%, 20%, 25%, 30%, 35%, or 40% in about one day; no more than about 10%, 15%, 20%, 30%, 35%, 40%, 45%, 50%, 55%, or 60% in about two days; no more than about 30%, 35%, 40%, 45%, 50%, 55%, 60%, 65%, 70%, 75%, or 80% in about three days; and/or no more than about 40%, 45%, 50%, 55%, 60%, 65%, 70%, 75%, 80%, 85%, or 90% in about four days. In specific embodiments, expression is enhanced no more than about 30% in one day, no more than about 45% in about two days, no more than about 60% in about 3 days, no more than about 70% in about 4 days, and/or no more than about 90% in about 5 days. In a specific embodiment, expression is enhanced only about 25% in about one day, 30-40% in about two days, 40-60% in about three days, 50-70% in about four days, and/or 75-90% in about five days.

In another embodiment, at least two to ten days after dilution of ligand to a non-inhibitory concentration are required to reach maximal expression; in various embodiments at least three to about ten days; in various embodiments at least four to about ten days; in various embodiments at least five to about ten days. In various embodiments, 50% of maximal expression is not achieved until about two days; in various embodiments about 50% of expression is not achieved until about three days; in various embodiments about 50% of expression is not achieved until about four days.

In another aspect, the invention features an isolated nucleotide sequence encoding a regulatory fusion protein (RPR), wherein the fusion protein consists of (1) a transcription blocking domain capable of inhibiting expression of the nucleotide sequence of interest, and (2) a ligand-binding domain, wherein in the presence of a cognate ligand capable of binding the ligand-binding domain, the fusion protein is stabilized.

In separate embodiments, the transcription blocking domain may be derived from a bacterial, bacteriophage, eukaryotic, or yeast repressor protein. In more specific embodiments, the transcription blocking domain is derived from a bacterial or bacteriophage repressor protein, such as, for example, TetR, LexA, LacI, TrpR, Arc, and LambdaC1. In another embodiment, the transcription blocking domain is derived from a eukaryotic repressor protein, such as, for example, GAL4. In another specific embodiment, the transcription blocking domain is a mutated restriction enzyme capable of binding but not cleaving DNA, and the operator is a recognition site for the restriction enzyme. In this specific embodiment, for example, the transcription blocking domain is a mutated Not1.

In specific embodiments, the ligand-binding domain is derived from a steroid, thyroid, or retinoid receptor. In more specific embodiments, the ligand-binding domain is derived from an estrogen receptor, and the cognate ligand is an estrogen. In an even more specific embodiment, the estrogen receptor contains one or more mutations, for example, the T2 mutations, and the cognate ligand is tamoxifen.

In another aspect, the invention features a regulatory fusion protein (RPR) consisting of (1) a transcription blocking domain capable of inhibiting expression of the nucleotide sequence of interest, and (2) a ligand-binding domain, wherein in the presence of a cognate ligand capable of binding the ligand-binding domain, the fusion protein is stabilized. In a specific embodiment, the regulatory fusion protein (RPR) consisting essentially of (1) a transcription blocking domain capable of inhibiting expression of the nucleotide sequence of interest, and (2) a ligand-binding domain, wherein in the presence of a cognate ligand capable of binding the ligand-binding domain, the fusion protein is stabilized.

In another aspect, the invention features a eukaryotic cell capable of inducible expression of a nucleotide sequence of interest, comprising a nucleotide sequence encoding a regulatory fusion protein (RPR), wherein the fusion protein consists of (1) a transcription blocking domain capable of inhibiting expression of the nucleotide sequence of interest, and (2) a ligand-binding domain; (ii) a promoter operably linked to the nucleotide sequence of interest and controlled by an operator that binds the fusion protein, and (iii) an operator capable of binding the transcription blocking domain and blocking transcription from the adjacent promoter. In a specific embodiment, the eukaryotic cell the fusion protein consists essentially of (1) a transcription blocking domain capable of inhibiting expression of the nucleotide sequence of interest, and (2) a ligand-binding domain; (ii) a promoter operably linked to the nucleotide sequence of interest and controlled by an operator that binds the fusion protein, and (iii) an operator capable of binding the transcription blocking domain and blocking transcription from the adjacent promoter.

In another aspect, the invention features a transgenic animal comprising a eukaryotic cell capable of inducible expression of a nucleotide sequence of interest, comprising a nucleotide sequence encoding a regulatory fusion protein (RPR), wherein the fusion protein consists of (1) a transcription blocking domain capable of inhibiting expression of the nucleotide sequence of interest, and (2) a ligand-binding domain; (ii) a promoter operably linked to the nucleotide sequence of interest and controlled by an operator that binds the fusion protein, and (iii) an operator capable of binding the transcription blocking domain and blocking transcription from the adjacent promoter.

Other objects and advantages will become apparent from a review of the ensuing detailed description.

BRIEF DESCRIPTION OF THE FIGURES

FIG. 6 is a schematic diagram of the CMV-MIE/AO hybrid promoter (SEQ ID NO:6, top strand) having tandem arc operators immediately downstream of the CMV-MIE promoter/enhancer (TATA box).

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, references to "a method" include one or more methods, and/or steps of the type described herein and/or that will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

The present invention is based in part on the concept that gene expression in eukaryotic cells can be tightly regulated using a strong promoter that is controlled by an operator that is in turn regulated by a regulatory fusion protein (RFP). The RFP consists essentially of a transcription blocking domain, and a ligand-binding domain that regulates its activity. In the presence of the cognate ligand for the ligand-binding domain, the RFP binds the operator thereby preventing transcription of the GOI. When the cognate ligand is withdrawn, the RFP is destabilized and transcription of the nucleotide sequence of interest proceeds.

Figure 4:
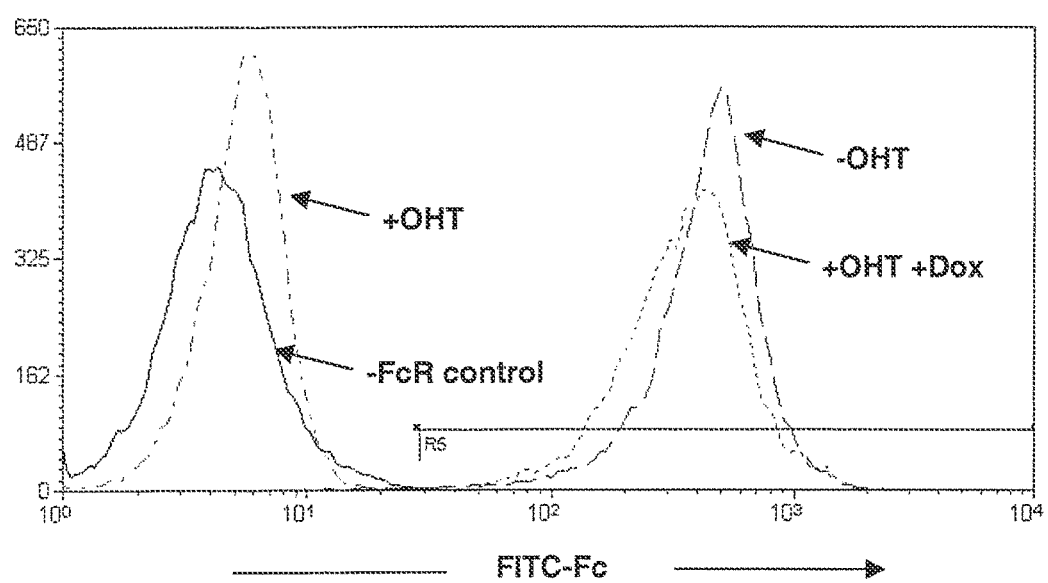
FIG. 4 show flow cytometry histograms of CHO K1-FcR/pTE313 clone D124 grown in the presence or absence of OHT, or in the presence of OHT and Dox, stained with FITC-Fc.
Figure 7:
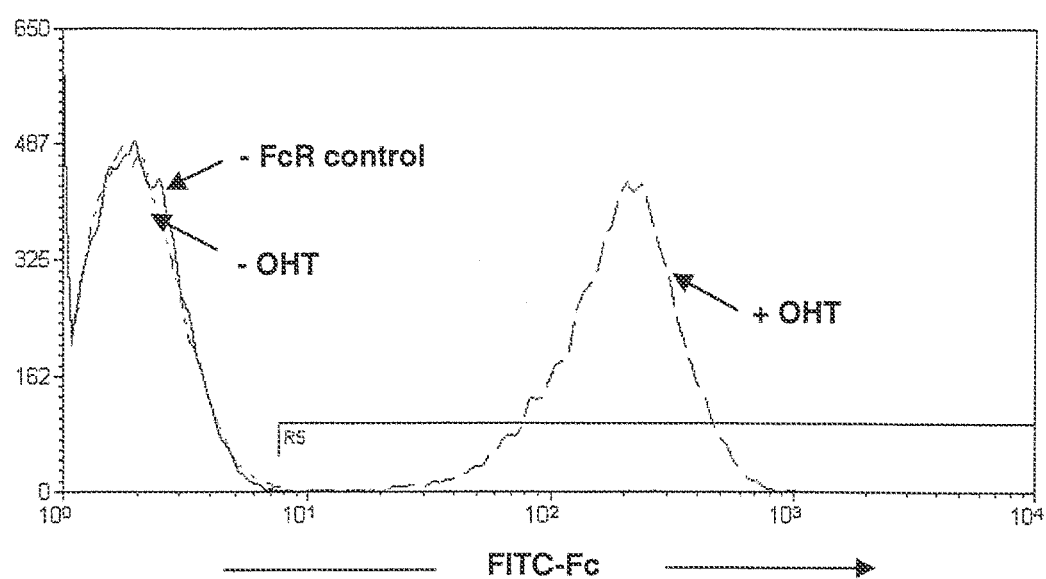
FIG. 7 show flow cytometry histograms of CHO K1-FcR/pTE534 clone C17 grown in the presence or absence of OHT, stained with FITC-Fc.

The regulatory system described herein provides specific advantages that combine a tightly regulated control of expression of a nucleotide sequence of interest with the isolation of cell lines capable of high level expression of the nucleotide sequence of interest suitable for large scale production. The term "tightly regulated" is meant that in the presence of a ligand that binds the ligand binding domain of the fusion protein of the invention, transcription of the nucleotide sequence of interest is substantially reduced, e.g., for example, at least a 20-fold decrease in transcription is achieved in the presence of the ligand relative to the level of transcription seen in the absence of the ligand. In more specific embodiments, the method of the invention achieves at least a 50-fold decrease in transcription in the presence of ligand. In even more specific embodiments, the method of the invention achieves a 100-fold or greater decrease in transcription in the presence of ligand. Examples of the degree of transcription control achieved by the methods of the invention are seen in FIGS. 4 and 7. The degree of regulation of transcription achieved by the method of the invention may also be stated as a difference in the expression of the nucleotide sequence of interest in the absence of the ligand is at least 20-fold greater, preferably at least 50-fold greater, more preferably at least 100-fold greater, than expression of the nucleotide sequence of interest in the presence of the ligand.

Isolation of cell lines capable of expressing a nucleotide sequence of interest at high levels requires tight regulation, but induction of the nucleotide sequence of interest expression is preferably accomplished by removal of an inducer, rather than the addition of one, is of substantial commercial importance as a means of reducing the cost of production relative to a system that requires the addition of a ligand during large-scale production. The present invention describes a regulatory system that satisfies these requirements.

Nucleotide Sequence of Interest

The methods of the invention may be broadly used to control the transcription of any nucleotide sequence of interest. The method of the invention may be used to produce a desired protein or protein fragment, including, for example, fusion and chimeric proteins or peptides. Further, the product of interest may be a transcription product, e.g., an mRNA or catalytically active RNA, or a downstream product resulting from the action of the initial transcription product.

Proteins of interest may include, without limitation, a hormone, a receptor or receptor fragment, an antibody or antibody fragment, a biologically active peptide or protein, an enzyme, a repressor protein, or a DNA binding protein.

Promoters

"Promoter" as used herein indicates a DNA sequence sufficient to direct transcription of a DNA sequence to which it is operably linked, i.e., linked in such a way as to permit transcription of the nucleotide sequence of interest when the appropriate signals are present. The expression of a nucleotide sequence of interest may be placed under control of any promoter or enhancer element known in the art.

Useful promoters that may be used in the invention include, but are not limited to, the SV40 early promoter region, the promoter contained in the 3' long terminal repeat of Rous sarcoma virus, the regulatory sequences of the metallothionein gene, mouse or human cytomegalovirus IE promoter (Gossen et al., (1995) Proc. Nat. Acad. Sci. USA 89:5547-5551); plant expression vectors comprising the nopaline synthetase promoter region, the cauliflower mosaic virus 35S RNA promoter, and the promoter of the photosynthetic enzyme ribulose biphosphate carboxylase; promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I; insulin; immunoglobulin; mouse mammary tumor virus; albumin; α-fetoprotein; α1-antitrypsin; β-globin; and myosin light chain-2.

Operators

As used herein "operator" indicates a DNA sequence that is introduced in or near a gene in such a way that the gene may be regulated by the binding of the RFP to the operator and, as a result, prevent or allow transcription of the GOI. A number of operators in prokaryotic cells and bacteriophage, have been well characterized (Neidhardt, ed. *Escherichia coli* and *Salmonella*; Cellular and Molecular Biology 2d. Vol 2 ASM Press, Washington D.C. 1996). These include, but are not limited to, the operator region of the LexA gene of *E. coli*, which binds the LexA peptide and the lactose and tryptophan operators, which bind the repressor proteins encoded by the LacI and trpR genes of *E. coli*. These also include the bacteriophage operators from the lambda $P_R$ and the phage P22 ant/mnt genes which bind the repressor proteins encoded by lambda cl and P22 arc. In an alternative embodiment, when the transcription blocking domain of the RFP is a restriction enzyme, the operator is the recognition sequence for that enzyme. One skilled in the art will recognize that the operator must be located adjacent to, or 3' to the promoter such that it is capable of controlling transcription by the promoter. For example, U.S. Pat. No. 5,972,650, which is incorporated by reference herein, specifies that tetO sequences be within a specific distance from the TATA box. In specific embodiments, the operator is preferably placed immediately downstream of the promoter. In other embodiments, the operator is placed within 10 base pairs of the promoter.

Transcription Blocking Domain

As used herein, a transcription blocking domain is any domain capable of blocking transcription as a result of its interaction with an operator. Such a domain may be derived from bacteria, bacteriophage, or yeast, and includes, but is not limited to, those repressors, or derivatives thereof, whose function depends upon ligand binding, such as TetR, LexA, LacI and Arc. Alternatively, the transcription blocking domain may be derived from mammalian cells as described, for example, in Yin et al. 1995 J. Virol. 69:6209-6218 or plant cells, as described, for example, in Wilde et al. 1994 Plant Mol. Biol. 24:38. The transcription blocking domain may also be made synthetically. For example, the transcription blocking domain may be a restriction enzyme that is mutated such that it can no longer cleave DNA. In such a case, the recognition sequence for that enzyme would be used as the operator.

Ligand-Binding Domain

While the ability of the fusion protein to interact with the operator is controlled by the transcription blocking domain, the activity of the fusion protein is regulated by the ligand-binding domain. The ligand-binding domain can be derived from any polypeptide that, when bound to its cognate ligand, renders the polypeptide functional, including for example, stabilizing the polypeptide. The ligand-binding domain is meant to include naturally occurring ligand-binding domains, as well as functional derivatives thereof. As used herein, "cognate ligand" includes the naturally occurring ligands that bind the ligand-binding domains, as well as functional derivates thereof. Examples of such ligand-binding domains include, but are not limited to, the ligand-binding domains of steroid receptors glucocorticoid receptors, retinoid receptors and thyroid receptors (Eilers et al. (1989) Nature 340:66-68; Picard et al. (1988) Cell 54:1073-1080). Examples 1-3 illustrate one embodiment of the invention, in which the transcription blocking domain of the fusion protein is TetR and the ligand-binding domain is the estrogen receptor ligand-binding domain with T2 mutations ($ER_{LBD}T2$; Feil et al. (1997) Biochem. Biophys. Res. Commun. 237:752-757). When tetO sequences were placed downstream and proximal to the strong CMV-MIE promoter, transcription of the nucleotide sequence of interest (in this case hFcγRI) from the CMV-MIE/tetO promoter was blocked in the presence of tamoxifen and unblocked by removal of tamoxifen.

Cell Selection Methodologies

The methods of the invention produce cells having a high production rate for a nucleotide sequence of interest. In addition to the methods described in the experimental section below, a variety of selection processes known to the art may be used. In one preferred embodiment, the selection process is the "FASTR" methodology described in USSN 20020168702 published 14 Nov. 2002, herein specifically incorporated by reference. The FASTR methodology is a high-throughput screening method for rapid isolation of cells secreting a cytokine-specific fusion protein of the invention, by direct screening of the fusion protein.

Cell Culture

In many applications, it is desirable to maximize cell density by repressing or preventing expression for some period of time while the cells in culture multiply, so that the culture can achieve a desirably high density (e.g., maximal, or near maximal, cell density). This is because non-induced cells will typically grow to a higher density in culture than induced cells, although in many circumstances the growth rate of non-induced cells (i.e., the time taken to achieve maximal achievable density for the non-induced cells, or change in culture density with time), compared with the growth rate of induced cells (i.e., the time taken to achieve maximal achievable density for the induced cells, or change in culture density with time), can be about the same. Following a time period of repressed or inhibited expression while the cells grow to a desired density, an inducer is typically added to the culture. When the inducer is added to the culture, the cells begin to express the protein of interest. In this way, a desirably high cell density is achieved prior to induction so that the culture yields a desirable amount of the induced protein of interest.

Methods and compositions are provided to facilitate inducing expression of a protein of interest in a cell culture, for example, in a bioreactor, wherein the induction does not require the addition of an inducer. Further, methods and compositions for achieving a delayed induction of expression of cells in culture are also provided. A delayed induction includes induction of a desired level of expression of a protein of interest only after or at a point in time after which cells have grown to a desired density. In general, under some circumstances, it is desirable to allow cells to reach a desired density, e.g., about 30, 40, 50, 60, 70, 80, 90, or 100% of maximal achievable density in culture, before a desired amount of induction of expression of the protein of interest occurs. In some embodiments, a cell density of about 90 to about 100% is desirable prior to full induction of a protein of interest. In some embodiments, no substantial induction is achieved until maximum cell density is reached. In some embodiments, a pre-induction period wherein the ligand is present at a sub-maximally inhibiting concentration and the cells are present at a density less than a maximal density is conducted. Following the pre-induction period, for example when cells in a pre-induction stage reach about maximal density, the cells are then diluted into a larger culture, wherein the concentration of the ligand in the larger culture is a concentration that no longer support substantial inhibition or inhibition of expression of the protein of interest. Yield of the protein of interest (amount of protein of interest per liter of culture) can be enhanced substantially if induction is delayed until maximum cell density is attained. In various embodiments, yield of the protein of interest is about 1-2 g/l, 2-3 g/l, about 2-5 g/l, about 3-6 g/l, or about 4-8 g/l, with respect to liter of cell suspension at about a maximal cell density and about maximal induction of the protein of interest.

Delayed induction can be achieved by any suitable combination of the compositions and methods disclosed herein. In various embodiments, delayed induction can be achieved by growing cells to a desired cell density in the presence of a selected concentration of the ligand that inhibits expression of the protein of interest, then removing the ligand that prevents expression of the protein of interest. The removing of the ligand can be achieved by, for example, separating the cells from media containing the ligand, diluting the cells with media that does not contain the ligand, and splitting or diluting a mixture of the cells and media such that the ligand is then present at a suitably low concentration (e.g., a concentration of the ligand that does not substantially inhibit, or fails to inhibit, expression of the protein of interest). In various embodiments, cells are initially grown and/or stored (e.g., in a master cell bank (MCB)) in a concentration of the ligand (e.g., tamoxifen, for a regulatory fusion protein comprising an estrogen ligand-binding domain or modification thereof) sufficient to inhibit expression of the protein of interest through a series of dilutions until reaching a desired culture size (e.g., a 3,000 or a 10,000 liter bioreactor). Once the desired culture size is reached, the concentration of the ligand should fall below an inhibitory amount, thus allowing expression of the protein of interest. In various embodiments, the original concentration of ligand is selected so as to reach a non-maximally inhibiting level in the penultimate dilution, and reach a non-inhibiting concentration in the final dilution (e.g., non-maximally inhibiting at 3,000 liters, and non-inhibiting at 10,000 liters). In these embodiments, the cells experience a "pre-induction" in the penultimate dilution (e.g., at 3,000 liters), and a full induction at 10,000 liters.

The inhibitory effect of the presence of the ligand is reduced by lowering the concentration of the ligand with respect to the cell density. Although the lower concentration can be achieved through dilution alone, it is believed that increases in cell density in culture are also at least in part responsible for expression of the protein of interest. Although cells are diluted in media that does not contain the ligand (e.g., from a 500 liter bioreactor to a 3,000 liter bioreactor; from a 3,000 liter bioreactor to a 10,000 liter bioreactor), and the concentration of ligand can thus fall to below a substantially inhibitory concentration at the initial cell density, the growth of cells at a more or less fixed (e.g., low) concentration of the ligand will generally result itself in a reduction of the ability of the ligand to inhibit expression of the protein of interest in the culture. That is, the system herein is such that expression of the protein of interest is expected to increase as cell density increases, at a fixed sub-optimally inhibiting concentration of ligand, since there are more and more cells due to cell division as time advances. Thus with this disclosure in hand, the system can be designed such that a minimal or non-inhibiting concentration of ligand is reached as cells approach a maximal or desirable density.

In various embodiments, expression of the protein of interest by removing a ligand allows for a relatively slow, or controlled, expression of the protein of interest as compared to adding an inducer. The slow or controlled expression is advantageous because the cells in culture are allowed to grow to a suitable cell density in the absence of an immediate and undesirably high level of induction of the protein of interest. Because the process is slower than would be observed by simply employing a system with positive induction and adding an inducer, cells are able to grow relatively unimpeded by the demand for producing high levels of protein as they grow in a minimally-inhibiting or non-inhibiting concentration of the ligand. This will generally allow the cells to grow to a higher density, and will generally result in a satisfactory yield of protein of interest per volume of culture, frequently higher than would be observed with other (i.e., positive) induction systems or constitutive expression systems.

Many applications can benefit from a system wherein induction of expression of a protein of interest in a cell culture is achieved without the need for adding an inducer to the cell culture. These benefits include, for example, obviating contamination risks associated with adding the inducer to the cell culture. Further, since there is no need to add an inducer, reproducibility can be improved since variations or errors in inducer concentration or variations in the quality of inducer preparations are eliminated. In particular, there are benefits to the methods described herein when growing cells in large bioreactors, on the order of, for example, 50 liters, 500 liters, 3,000 liters, and 10,000 liters.

Figure 10:
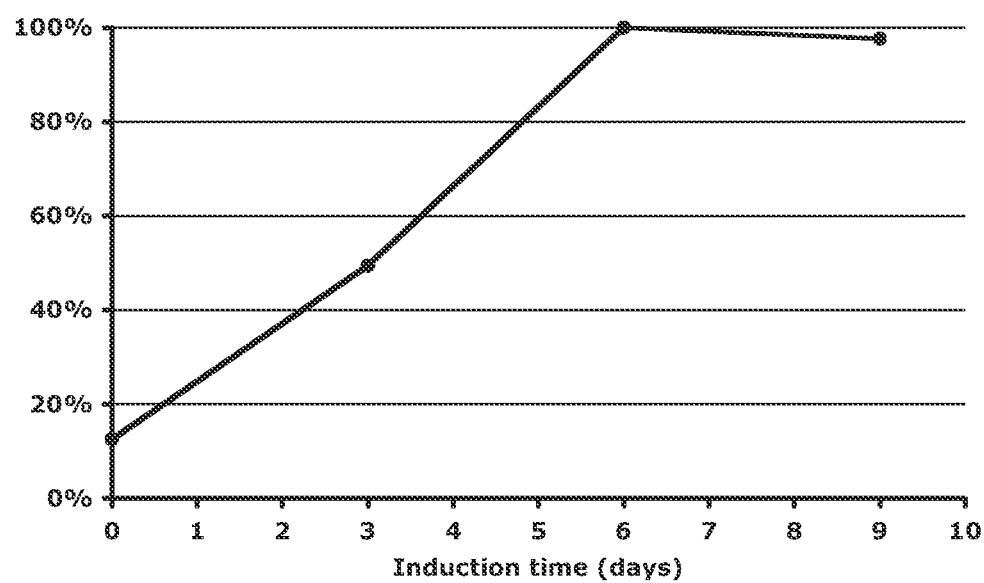
FIG. 10 illustrates the relative expression of 13SC1132 for 9 days following induction (i.e., removal of OHT).

Although different cells and different clones (e.g., different clones of a eukaryotic cell comprising the regulator fusion protein and a gene for a protein of interest) may have somewhat different growth curves or different induction times, the methods described allow those skilled in the art to achieve induction at a desired cell density or point in time. For example, for a given clone, a person of skill could readily determine induction time as shown in FIG. 10, develop a suitable manufacturing seed train as shown in FIG. 11A, employ a curve as in FIG. 12 to select a suitable concentration of ligand for the culture, determine the batch day for cumulative specific productivity with different pre-incubation times and determine titer at a selected pre-induction times as in FIGS. 13-14 in order to achieve a desired delay in induction (or maximal induction) of a protein of interest in culture employing the regulatory fusion protein and system described herein.

In various embodiments, cells comprising the regulatory fusion protein are banked at a high cell density in a master cell bank (MCB) in the presence of excess ligand, for example, from 100 nanomolar to 10 micromolar OHT. Cells can alternatively, or also, be diluted or expanded in a medium containing excess ligand, for example, from 100 nanomolar to 10 micromolar. In one embodiment, the OHT concentration is selected so as to fully or substantially inhibit expression of the protein of interest throughout the seed train (e.g., according to FIG. 11A and FIG. 11B) until the final bioreactor step, i.e., until the culture reaches the 10,000 liter bioreactor. In another embodiment, OHT is added to the medium in the 10 liter Wave™ bag, an no OHT is added beyond the 10 liter Wave™ bag step. In another embodiment, a concentration of OHT is selected so as to fully or substantially inhibit expression of the protein of interest to the 500 liter bioreactor stage, but not the 3,000 liter and 10,000 liter bioreactor stages, such that a pre-induction in the 3,000 liter bioreactor is achieved. In one embodiment, the OHT concentration is selected such that the pre-induction stage is one day, two days, three days, four days, or five days. In various embodiments, the pre-induction occurs at concentration of OHT wherein specific productivity is about 50, 60, 70, 80, 90, or 100% of specific productivity in the absence of OHT.

Examples of suitable concentrations of ligand (e.g., OHT) in the master cell bank or the first seeded culture (e.g., a 10 liter Wave™ bag used in a seed train for a 10,000 liter bioreactor) include about 100 nM to about 1,000 nM, about 100 to 900 nM, 100 to 800 nM, about 100 nM to 700 nM, 100 nM to 600 nM, 100 nM to 500 nM, 100 nM to 400 nM, 100 nM to 300 nM, in a specific embodiment about 200 nM to about 500 nM, in another specific embodiment, about 400 nM.

Figure 11A:
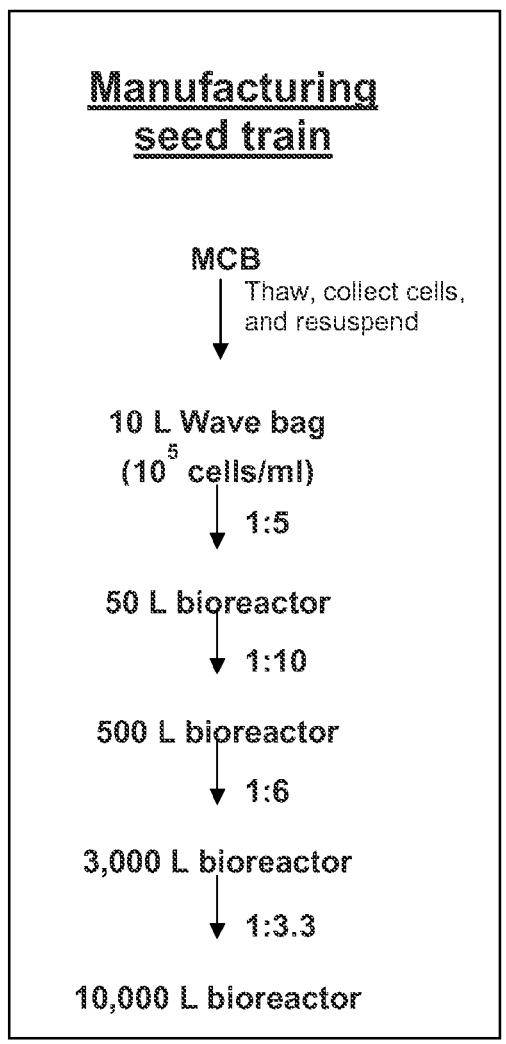
FIG. 11A and FIG. 11B show a manufacturing seed train (FIG. 11A) modeled by a bench top induction model (FIG. 11B).

In a specific embodiment, a protein of interest is expressed from a cell line comprising a gene encoding the protein of interest whose expression is controlled by a regulator fusion protein as described herein (capable of binding OHT), wherein the cell is a CHO cell, and the cell line is propagated in a seed train according to FIG. 11A, wherein the concentration of OHT in the 10 liter Wave™ bag step is 100-500 nM, or about 400 nM, wherein the concentration of OHT is reduced so as to allow for a pre-induction phase at the 3,000 liter bioreactor stage, and wherein maximal induction occurs in the 10,000 liter bioreactor.

Transgenic Animals

The present invention also contemplates the creation of transgenic mammals that express the fusion proteins of the invention. For example, it may be desirable to regulate the expression of nucleotide sequence of interest in a mammal. A gene encoding the fusion proteins of the invention may be integrated into the genome of a mammal so as to regulate the expression of a nucleotide sequence of interest whose promoter was engineered to be responsive to the fusion protein. Further, transgenic animals may be useful as a source of a nucleotide sequence of interest.

A transgenic animal can be produced by introducing a nucleic acid construct into the male pronuclei of a fertilized oocyte, e.g., by microinjection, retroviral infection, and allowing the oocyte to develop in a pseudopregnant female foster animal. Any of the regulatory or other sequences useful in expression vectors can form part of the transgenic sequence. A tissue-specific regulatory sequence(s) can be operably linked to the transgene to direct expression of the transgene to particular cells.

Kits

The invention also provides a kit comprising one or more containers filled with at least one fusion protein of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Figure 1:
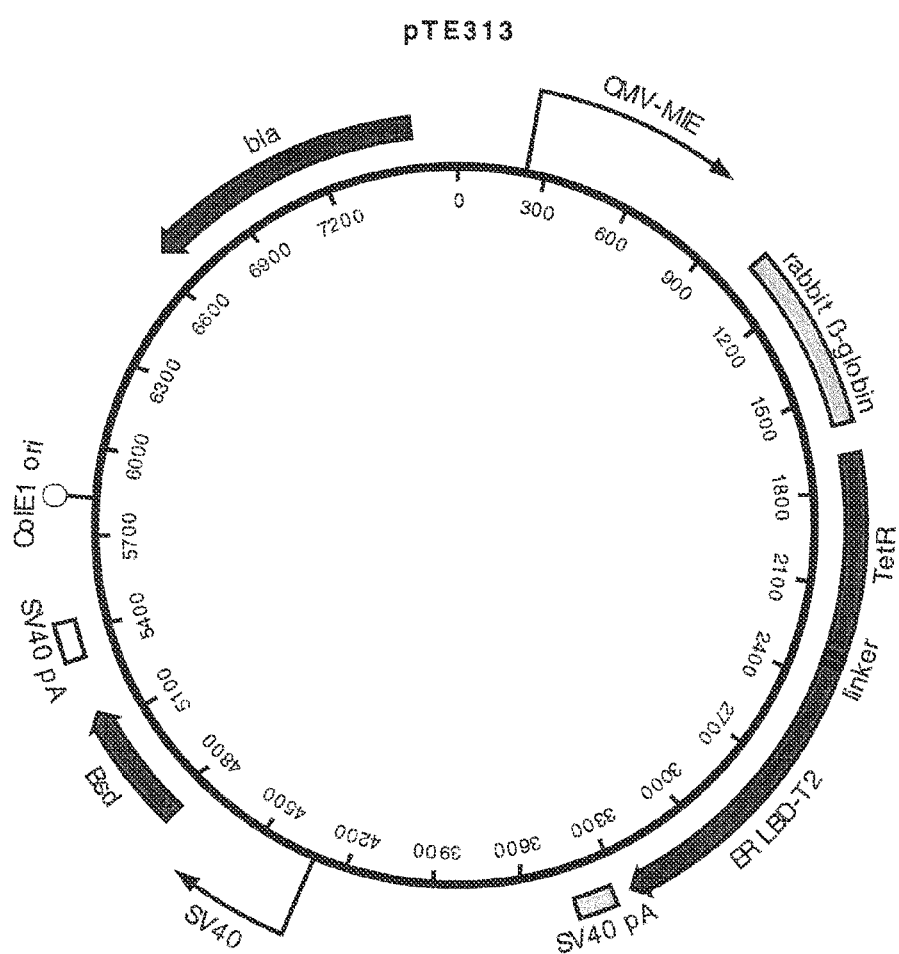
FIG. 1 represents the structure of pTE313, designed for the expression of TetR-ER$_{LBD}$T2 from the CMV promoter.
Figure 2:
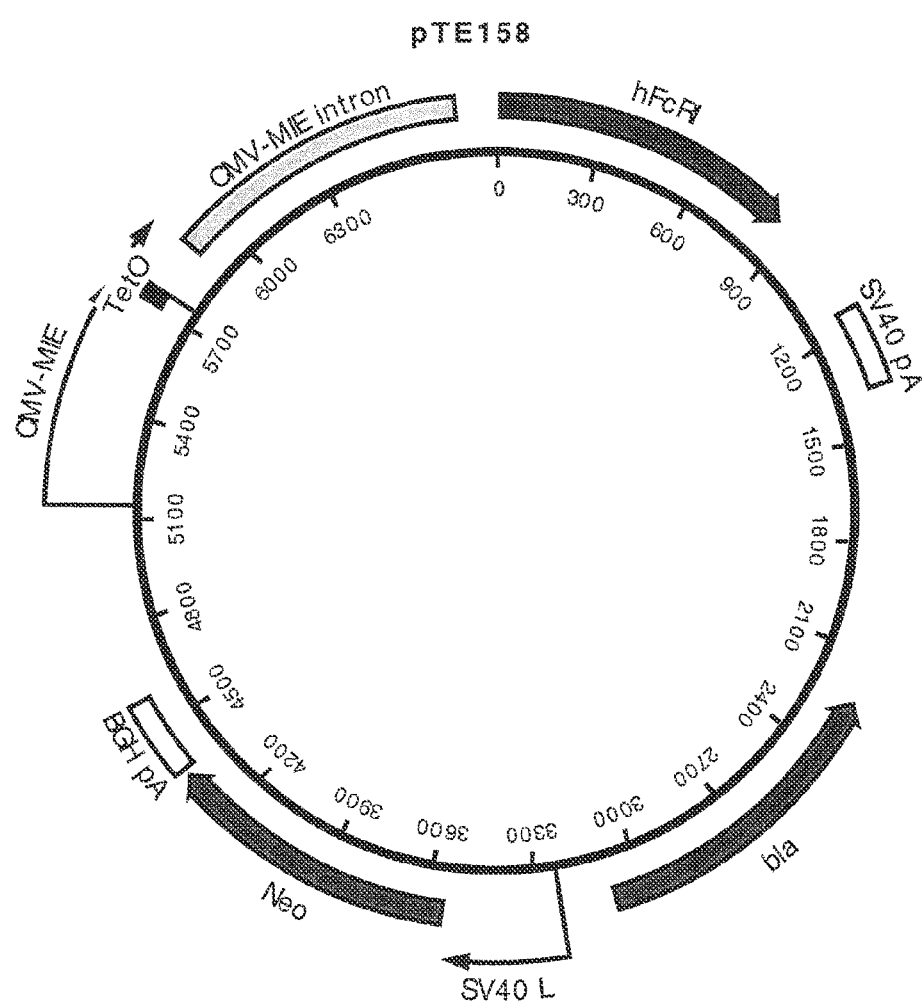
FIG. 2 represents the structure of pTE158, designed for the expression of human FcγRI from a CMV promoter that is regulated by the tetracycline repressor.

Example 1 describes construction of the pTE313, pTE084, and pTE158 plasmids. pTE313 designed for high-level expression of a regulatory fusion protein TetR-$ER_{LBD}$T2. It contains a first independent expression cassette that is the TetR-$ER_{LBD}$T2 fusion gene driven by the CMV-MIE promoter, and the second independent cassette that is the blasticidin resistance gene driven by the SV40 promoter (FIG. 1). pTE084 was designed for the high level expression of hFcγRI, the high affinity cell surface receptor for the Fc domain of human IgG. pTE158 was generated by placing two tandem TetR operator immediately downstream of the CMV-MIE promoter/enhancer in pTE084 (FIG. 2). CHO K1 cells expressing the hFcγRI gene regulated by the TetR-$ER_{LBD}$T2 RFP after transfection with pTE313 were generated and identified as described in Example 2.

Figure 3:
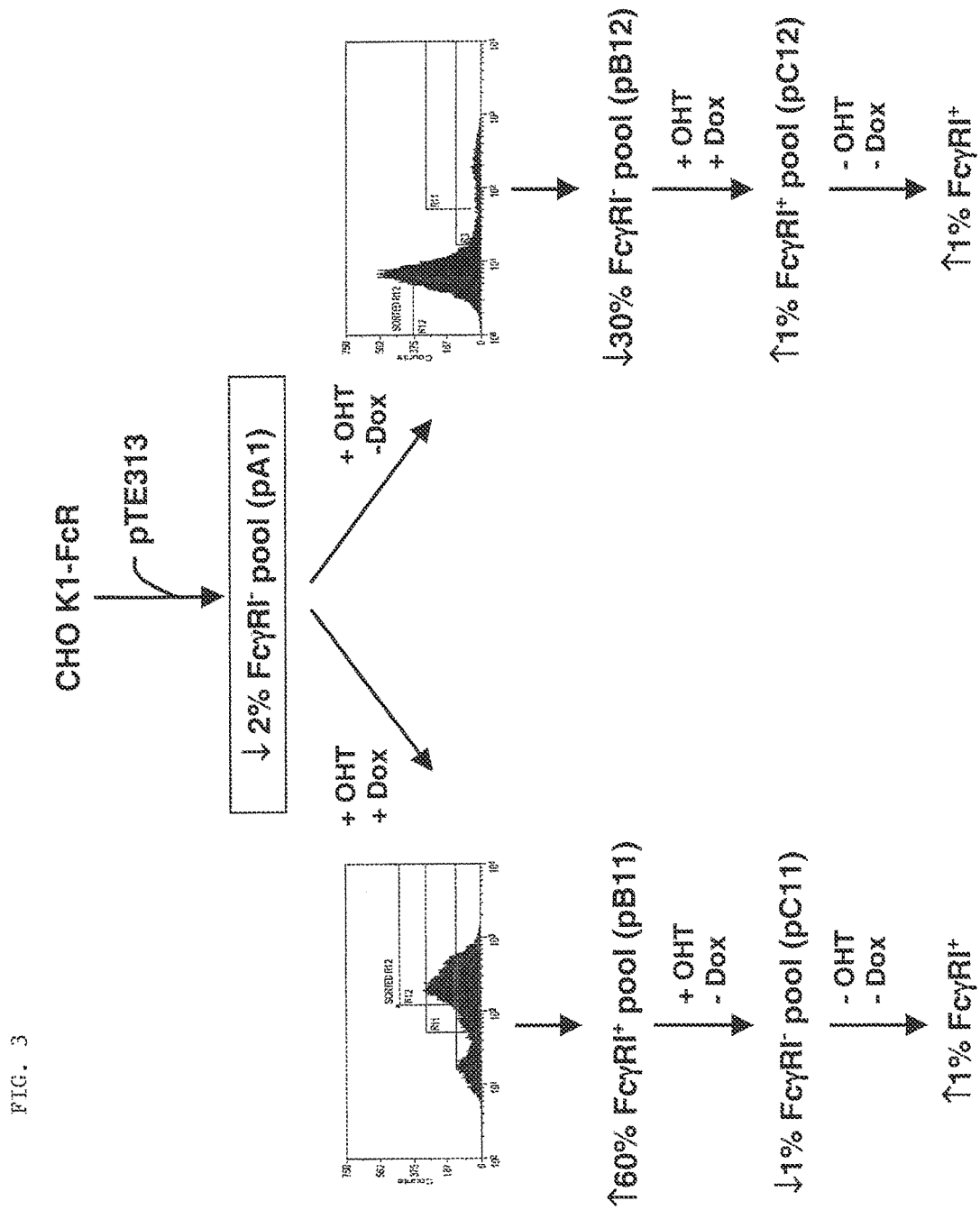
FIG. 3 shows an outline of the two strategies used to isolate CHO K1 clones that expressed the hFcγRI gene regulated by the TetR-ER$_{LBD}$T2 RFP.

Two strategies were employed to isolate clones that expressed the hFcγRI gene regulated by the TetR-$ER_{LBD}$T2 RFP after transfection with pTE313 (FIG. 3). Both strategies started from the same pool of cells obtained after introduction of the TetR-$ER_{LBD}$T2 RFP into CHO K1-FcR cells and isolation (Example 3). These results clearly show that the expression of a recombinant gene can be tightly regulated by TetR-$ER_{LBD}$T2 and induction of expression can be achieved by either the addition of doxycycline in the presence of tamoxifen or the removal of tamoxifen (FIG. 4). Induction of the expression of a nucleotide sequence of interest by removal of a small molecule from the culture medium, easily achieved by dilution or medium exchange, provides a cost-effective means to induce expression at large scale. Moreover, these data show that tight regulation of expression can be achieved by the TetR-$ER_{LBD}$T2 regulatory fusion protein.

CHO K1 cells expressing hFcγRI driven by CMV-MIE/ArcO2 promoter were generated as described in Examples 4 and 5. Inducible cell lines regulated by Arc-$ER_{LBD}$T2 were selected similar to the strategies shown in FIG. 3, and showed tight regulation in response to the presence of OHT in the growth medium (Example 6 and FIG. 7).

The methods and compositions described herein can be advantageously used to express a protein of interest in a bioreactor, for example, a large scale bioreactor having a capacity of tens or hundreds or thousands or tens of thousands of liters. The fusion proteins, nucleotide sequences, cell lines, and systems described herein are particularly useful for bioreactor processes for expressing proteins. Non-limiting examples for adapting the methods and compositions described herein to large scale bioreactors are described herein.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Construction of pTE313, pTE084 and pTE158 pTE313 was constructed by ligating a 975 bp EcoR I fragment (blunted) from pTA-ER-LBD-T2 that encodes the human estrogen receptor ligand binding domain with T2 mutations ($ER_{LBD}T2$) (Feil, et al. 1997 Biochem Biophys Res Commun 237:752-757) into the EcoR I site (blunted, in the linker region immediately following the TetR C-terminus) of pcDNA6/TR (Invitrogen Cat. no. V-1025-20). The T2 mutations G400V, M543A, and L544A confer specificity for binding the estradiol analog tamoxifen. The proper orientation of the fragment encoding $ER_{LBD}T2$ in desirable plasmids resulting from the ligation was confirmed by DNA sequence determination. This construction resulted in a gene encoding a fusion protein consisting of amino acids M1 to S207 of TetR (SEQ ID NO:7) fused to a ligand-binding domain comprising amino acids N304 to V595 of the estrogen receptor (SEQ ID NO:8). The chimeric protein encoded by this gene also has the T2 mutations G400V, M543A, and L544A in the estrogen receptor. Plasmid pTE313 contains a cassette that is the $TetR-ER_{LBD}T2$ fusion gene driven by the CMV-MIE promoter, and a second cassette that is the blasticidin resistance gene driven by the SV40 promoter (FIG. 1).

pTE084 was constructed by ligating the 1,436 bp Xba I fragment from pCAE100 that encodes the human FcγRI (GenBank accession number M21091) into the Xba I site of pRG821, a vector that encodes the neomycin phosphotransferase II (npt) gene that confers resistance to G418. The orientation of hFcγRI in desirable plasmids resulting from the ligation was examined by restriction mapping with Not I, Pst I, Eco RI, and Stu I. A DNA fragment encoding two tandem TetR operators were placed immediately downstream of the CMV-MIE promoter/enhancer in pTE084 to generate pTE158 (FIG. 2). In this plasmid, transcription of hFcγRI from the CMV-MIE promoter was regulated by TetR or $TetR-ER_{LBD}T2$.

Example 2

Construction of a CHO K1 Derivative that Expresses hFcγRI Driven by CMV-MIE/tetO CHO K1 cells ($3 \times 10^6$ cells) were transfected with pTE158 using Lipofectamine™ (Life Technologies; Rockville, Md.) following the manufacturer's suggestions. The cells were placed in the culture medium (10% fetal bovine serum, 90% Ham's F-12, 2 mM L-glutamine; all reagents were from Life Technologies, Rockville, Md.) containing 500 μg/ml G418 (Life Technologies) for 12 days. Cells resistant to G418 were trypsinized, pooled, and stained with FITC-conjugated human IgG, Fc fragment (FITC-hFc; Jackson ImmunoResearch Laboratories, West Grove, Pa.). Briefly, cells grown on 10 cm culture plates were washed once with Dulbecco's phosphate-buffered saline (PBS) without calcium chloride and magnesium chloride (Life Technologies). Two milliliters of 0.25% trypsin (Life Technologies) was added to each plate and incubated at 37° C. for 4-5 min. The plates were swirled until the cells detached from the plate. Four milliliters of culture medium was immediately added to each plate of the detached cells. The cells were then collected by centrifugation at 1,000×g for 4 minutes then resuspended in 4 ml of 2 μg/ml FITC-hFc diluted in culture medium. The cells were then placed on a platform shaker and stained for one hour at room temperature. To remove unbound FITC-hFc, the cells were washed twice with 8 ml PBS. Washed cells capable of binding FITC-hFc were measured by flow cytometry on a MOFLO™ cell sorter (Cytomation; Fort Collins, Colo.). The FITC-hFc did not stain nontransfected parental CHO K1 cells but gave rise to a distribution of fluorescence in the G418-resistant, pTE158-transfected pool. The total pool of fluorescent cells from the G418-resistant population was collected by flow cytometry, expanded then analyzed by flow cytometry for expression of hFcγRI. Cells possessing the highest 15% fluorescence in this population were isolated, pooled, and expanded to yield a population of G418-resistant cells that expressed hFcγRI at high levels. This population of cells was named CHO K1-FcR and was used to isolate a clone that expressed the hFcγRI gene regulated by the $TetR-ER_{LBD}T2$ RFP after transfection with pTE313.

Example 3

Construction of CHO K1 Cell Lines with hFcγRI Expression Regulated by $TetR-ER_{LBD}T2$ CHO K1-FcR cells ($2 \times 10^6$ cells) were transfected with pTE313 using Lipofectamine™. The transfected cells were selected with 500 μg/ml G418 and 10 μg/ml blasticidin for 14 days to select for both plasmids, pTE158 and pTE313. Two days prior to analysis by flow-cytometry, cells were incubated in culture medium containing 200 nM 4-hydroxytamoxifen (OHT) to stabilize the activity of $TetR-ER_{LBD}T2$ and repress expression of hFcγRI. The cells were stained with FITC-hFc and those cells possessing the lowest 2% fluorescence, indicating repression of hFcγRI expression, were collected to yield pool A1. This pool was then used as the source of cells for the two strategies outlined in FIG. 3.

Clones that expressed hFcγRI regulated by $TetR-ER_{LBD}T2$ were isolated by manipulating the activity of $TetR-ER_{LBD}T2$ by the presence or absence of doxycycline (Dox). One strategy involved the isolation of cells expressing high levels of hFcγRI in the presence of OHT and Dox, followed by the isolation of non-expressing cells in the presence of OHT without Dox. Alternatively, cells expressing low levels of hFcγRI in the presence of OHT without Dox were first isolated, then high expressing cells were isolated from this pool by the induction with Dox in the presence of OHT. Both strategies utilized a series of cell isolations under alternating inducing or repressing conditions, and a final isolation of single cells that expressed high levels of hFcγRI in the absence of both OHT and Dox (FIG. 3).

Pool A1 was expanded for 7 days in the presence of 200 nM OHT, then split into two dishes; one dish contained medium with 1 μg/ml Dox and the other did not. Cells were incubated for three days then stained with FITC-hFc to detect the presence of hFcγRI. The top 60% of hFcγRI-positive cells from the culture induced with 1 μg/ml Dox were isolated to yield pool B 11, and cells with the lowest 30% fluorescence were isolated from cells grown in medium without Dox to yield pool B 12. Pool B 11 was grown in 200 nM 4-hydroxytamoxifen without Dox and the cells with the lowest 1% fluorescence were collected to yield pool C11. Pool B 12 was grown in 200 nM OHT and 1 µg/ml Dox, and the top 1% of hFcγRI-positive cells were collected as a pool to yield pool C12. Both pool C11 and pool C12 were then expanded in the absence of both OHT and Dox. Cells that expressed the highest levels of hFcγRI (top 1%) in the absence of OHT and Dox were then sorted onto 96 well plates at one cell per well. These cells should have low non-induced expression of hFcγRI and high levels of hFcγRI when induced by the removal of OHT as a consequence of alternating the isolation of induced or repressed hFcγRI expression.

After expansion, ten individual clones were characterized for the induction of hFcγRI, by withdrawal of OHT or addition of 1 µg/ml Dox, by immunostaining with FITC-hFc and analysis by flow cytometry. Analysis of one clone (D124 from pool C12) showed no detectable level of hFcγRI when OHT was present without Dox, whereas high levels of hFcγRI expression was observed in the absence of OHT and Dox. Furthermore, the addition of Dox at 1 µg/ml to cells grown in the presence of OHT also resulted in high levels of hFcγRI expression. The level of hFcγRI expression in this clone that resulted from induction by either removal of OHT or 1 µg/ml doxycycline, in the presence of OHT, were indistinguishable (FIG. 4).

Example 4

Construction of pTE528, pTE529, and pTE534

The phage P22 Arc repressor gene encodes a transcriptional repressor of 53 amino acids (M1 to A53 encoded by nucleotides 38,336 to 38,494 of the phage P22 genomic DNA (GenBank accession NC002371). Transcription repression mediated by Arc involves the sequential addition of dimers to operator half-sites. It was previously shown that a single chain dimer consisting of two Arc proteins connected by a 15 amino acid linker had higher affinity for arc operator DNA than the wild type repressor (Robinson et al. (1996) Biochemistry 35:109-116). To take advantage of the higher affinity of the single chain dimer for operator DNA, a synthetic DNA was designed that encoded this single chain Arc dimer fused a His tag sequence consisting of 6 histidine residues. This 444 bp synthetic XhoI/NotI DNA fragment was cloned into pUC 119 to yield pUC 119-Arc2-His6 (Blue Heron Technology Inc.). The Arc2 dimer gene was then excised from this plasmid and cloned into the XhoI and NotI sites of pRG985, such that expression of the Arc2 gene was dependent on the UbC promoter/β-globin intron, to yield pTE528.

Figure 5:
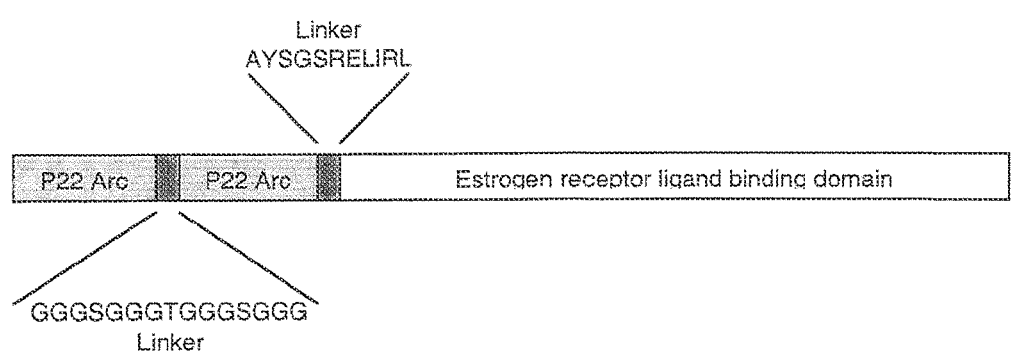
FIG. 5 is a schematic diagram of fusion protein Arc2-ER$_{LBD}$T2, with linkers GGGSGGGTGGGSGGG (SEQ ID NO:2) and AYSGRELIRL (SEQ ID NO:1).

The Arc2-ER$_{LBD}$T2 fusion protein (FIG. 5) was constructed by ligating a 3361 bp BamHI fragment from pTE502, that contains the human ER$_{LBD}$T2 encoding DNA as described above, into the BamHI sites of pTE528 to yield pTE529. The resulting Arc2-ER$_{LBD}$T2 fusion protein (SEQ ID NO:3) had the same 11 amino acid linker (AYSGSRE-LIRL) (SEQ ID NO:1) between the Arc2 gene and the ER$_{LBD}$T2 gene as between TetR and ER$_{LBD}$T2 in TetR-ER$_{LBD}$T2.

To change the Tet operators in CMV-MIE/TO promoter to Arc operators, base pairs 14,798-14,818 in the phage P22 genome (Genbank accession NC002371, SEQ ID NO:9), pTE158 was used as a template to amplify a DNA fragment by PCR with the following primer set (5'-GAGTATTTAC GGTAAACTGC CCACTT-3' (SEQ ID NO:4) and 5'-GA-GAGATCTG AGTCGACATA GTAGAGTGCT TCTAT-CATGA ATAGTAGAGT GCTTCTATCA TGAGCTCTGC TTATATAGAC CTCCCA-3') (SEQ ID NO:5). The PCR product, encoding tandem Arc operators was digested with NdeI and SalI and cloned into the same sites in pTE158. The CMV-MIE/AO hybrid promoter has two tandem arc operators immediately downstream of the CMV-MIE promoter/enhancer (FIG. 6) (SEQ ID NO:6). Consequently, the Arc2-ER$_{LBD}$T2 transcriptional repressor will regulate transcription of hFcγRI from the CMV-MIE/AO promoter in pTE534.

Example 5

Construction of a CHO K1 Derivative that Expresses hFcγRI Driven by CMV-MIE/ArcO2 Promoter CHO K1 cells (2×10$^6$) were transfected with pTE534 using Lipofectamine™ as described above. The cells were placed in the culture medium (10% fetal bovine serum, 90% Ham's F-12, 2 mM L-glutamine; all reagents were from Invitrogen Life Technologies, Carlsbad, Calif.) containing 400 µg/ml G418 (Invitrogen Life Technologies) for 12 days. Cells resistant to G418 were trypsinized, pooled, and stained with 2 µg/ml of FITC-conjugated human IgG, Fc fragment (FITC-hFc) as described above. The FITC-hFc did not stain nontransfected parental CHO K1 cells. Cells that expressed hFcγRI bound FITC-hFc and were isolated based on their fluorescence by flow cytometry on a MOFLO™ cell sorter. Cells with the highest 3% fluorescence in this population were isolated, pooled, and expanded. This hFcγRI-positive pool was enriched by repeating the cell surface staining with FITC-hFc and sorting the top 30% most fluorescent cells in the population to yield pool B. Cells in pool B that were among the top 20% expressing hFcγRI were isolated to yield pool C. Pool C2 (CHOK1/pTE534) was used to generate inducible cell lines regulated by Arc-ER$_{LBD}$T2.

Example 6

Construction of CHO K1 Cell Lines with Arc-ER-$_{LBD}$T2-Dependent hFcγRI Expression CHO K1/pTE534 cells (2×10$^6$/dish) were transfected with either pRG985, an empty vector, or pTE529 using Lipofectamine™ The transfected cells were selected with 400 µg/ml G418 and 10 µg/ml puromycin in the absence of OHT for 14 days. The cells were stained with FITC-hFc as described above and analyzed by flow cytometry. The cells transfected with pRG985 were similar to parental cells and had similar hFcγRI staining profiles whether or not they were grown in the presence of OHT prior to analysis. In contrast, the expression hFcγRI expression in CHO K1/pTE534 cells transfected with pTE529 show marked response to the presence of OHT in the growth medium. In the absence of OHT in the growth medium, the majority of G418 and puromycin-resistant cells were positive for hFcγRI expression, and the top 30% hFcγRI-positive cells were sorted as a pool. This pool was expanded in the presence of OHT for 10 days, stained for hFcγRI expression and analyzed by flow cytometry. Over 70% of the cells in this pool did not express hFcγRI in the presence of OHT, and those cells expressing the lowest 30% were sorted as a pool. These cells were then expanded in the absence of OHT in the medium. Cells that expressed the highest levels of hFcγRI (top 1%) in the absence of OHT were sorted into a 96-well plate at one cell per well.

Clones showing tight regulation in response to the presence of OHT in the medium were further characterized by flow cytometry. The OHT-dependent regulation of hFcγRI expression in these clones was confirmed by immunostaining with FITC-hFc followed by flow cytometry analysis. No detectable level of hFcγRI was observed in one clone (C17) when OHT was present in the medium, whereas growth in the absence of OHT induced expression of hFcγRI in these clones (FIG. 7).

Example 7

Figure 8:
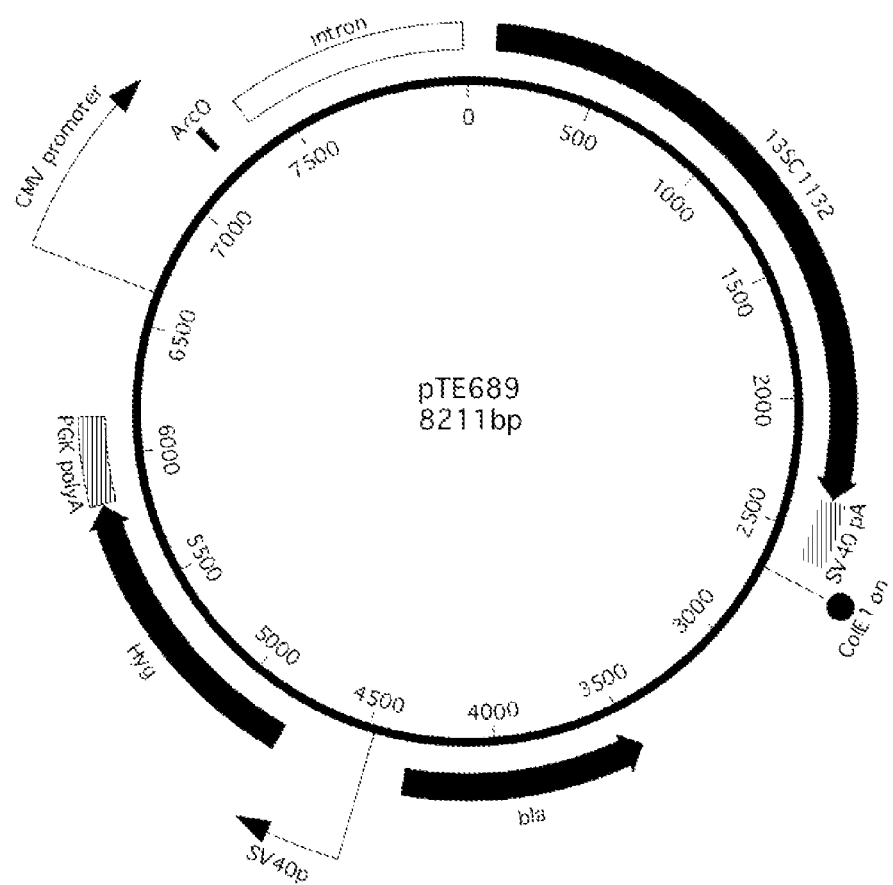
FIG. 8 is a diagram of the pTE689 construct comprising the fusion gene 13SC1132, a fusion of a cytokine receptor ligand-binding region and a human antibody heavy chain.

Construction of pTE689 pTE158 was used as a template to amplify a DNA fragment by PCR with the following primer set (5'-GAGTATTTAC GGTAAACTGC CCACTT-3' (SEQ ID NO:4) and 5'-GAGAGATCTG AGTCGACGAA TAGTAGAGTG CTTCTATCAT GAGCTCTGCT TATATAGACC TCCCA-3') (SEQ ID NO:10). The PCR product, encoding a single Arc operator, was digested with NdeI and SalI and cloned into the same sites in pTE534 to yield pTE633. The 1578 bp SpeI/HindIII DNA fragment from pTE633, containing the CMV-MIE/AO promoter was cloned into the SpeI/HindIII sites of pTE688, a plasmid encoding the 13SC1132 receptor-Fc gene (i.e., a gene encoding a polypeptide that is a fusion protein of a cytokine receptor ligand-binding region and a human antibody heavy chain, capable of dimerizing to form a protein having a human Fc that is capable of binding to FcγRI), such that expression of 13SC1132 is dependent on the CMV-MIE/AO promoter. The resulting plasmid was named pTE689 (FIG. 8).

Example 8

Construction of a CHO Cell Line that Expresses 13SC1132 Regulated by the Arc2-ER$_{LBD}$T2 Fusion Protein The RGC12 cell line was derived from CHO K1 and was engineered to conditionally express (expression in the presence of doxycycline) the human FcγRI high affinity Fc receptor for the purpose of quantitative cell surface display of proteins containing the human IgG Fc domain (see U.S. Pat. No. 7,435,553 and U.S. Pat. No. 6,919,183, incorporated herein by reference). This host cell line facilitates the isolation of single cells expressing antibodies or Fc-tagged proteins by flow cytometry based on the expression level of the secreted protein in each cell.

Figure 9:
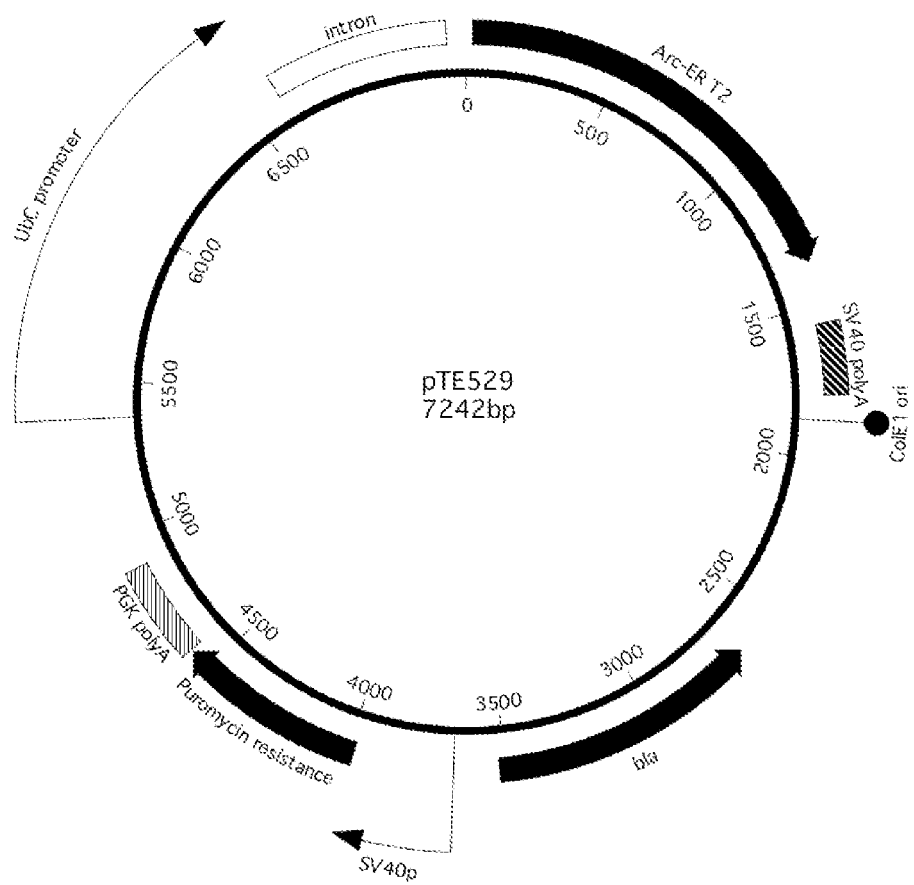
FIG. 9 is a diagram of pTE529, an expression construct form expressing the Arc-ERT2 regulatory fusion protein.

RGC12 cells ($2 \times 10^6$) were transfected with 5 mg pTE529 encoding the Arc-ER$_{LBD}$T2 protein driven by a ubiquitin promoter (FIG. 9) using Lipofectamine™ as described above. The cells were placed in the culture medium (10% fetal bovine serum, 90% Ham's F-12, 2 mM L-glutamine; all reagents were from Invitrogen Life Technologies, Carlsbad, Calif.) containing 10 µg/ml puromycin (CalBiochem) for 14 days. Cells resistant to puromycin, expressing the Arc2-ER$_{LBD}$T2 fusion protein, were then transfected with pTE689 encoding protein of interest 13SC11232 (FIG. 8) as described above except the culture medium contained 200 nM OHT. Cells containing stable integration of pTE689 were selected with 400 µg/ml hygromycin for 14 days. Hygromycin selection was maintained throughout the clone isolation process. Cells were subsequently grown in the absence of OHT for 10 days to induce expression of 13SC1132, then expression of hFcγRI was induced by the addition of 1 µg/ml of doxycycline to the culture medium, in the presence of one mg/ml rat IgG, one day prior to staining with polyclonal FITC-conjugated anti-human IgG (H+L) F(ab')$_2$ fragment and analysis by flow cytometry. Cells that secreted the highest levels of 13SC1132 as measured by 13SC1132 complexed with FcγRI on the cell surface (top 5%) were isolated by flow cytometry on a MOFLO™ cell sorter. Cells were grown in the presence of OHT for 7 days, and treated for screening as described above, but the cells with the lowest 5% cell surface fluorescence were isolated in order to enrich for clones with regulated expression of 13SC1132. Cells were then grown in the absence of OHT, treated for flow cytometry, and single cells with the highest 0.1% fluorescence in this population were isolated, expanded, and screened for 13SC1132 expression in the absence of OHT and tight regulation in the presence of OHT. One clone was chosen and renamed C110.

Example 9

Induction of 13SC1132 Expression by Removal of OHT

Induction of recombinant gene expression by removal of a small molecule is desirable over addition of a small molecule for large-scale bioreactor production as it obviates the addition of potentially expensive inducers and eliminates an opportunity for contamination to occur. To examine the feasibility of induction through removal of OHT by dilution, we first examined the time course of induction upon rapid removal of OHT.

The expression of 13SC1132 in clone C110 was determined at 3-day intervals after removal of OHT from the culture medium. In this experiment, the relative expression of 13SC1132 in the culture was determined by measuring the mean fluorescence of cell surface-displayed secreted protein as described in Example 8. Clone C110 was grown the presence of 400 µg/ml hygromycin and 200 nM OHT to repress expression of 13SC1132. Cells were isolated by centrifugation, washed in fresh medium without OHT or hygromycin, and then resuspended in fresh medium without OHT or hygromycin at $0.4 \times 10^6$ cells/ml in 30 ml. Cells were grown for 2 days at which time an aliquot of cells was removed to fresh medium containing 1 µg/ml doxycycline to induce hFcγRI expression for analysis by flow cytometry, then the cells were grown for an additional day prior to analysis. The remaining cells were reseeded in fresh media and grown for 2 days, then processed as described above such that the mean fluorescence of cells, resulting from the cell surface expression of 13SC1132, was determined 3, 6, and 9 days after OHT removal. The fully repressed expression level of 13SC1132 was determined by flow cytometry from cells grown it the presence of OHT. FIG. 10 shows that the rate of induction of 13SC1132 upon removal of OHT was slow, and that full induction of 13SC1132 expression was not observed until 6 days after OHT removal.

Figure 11B:
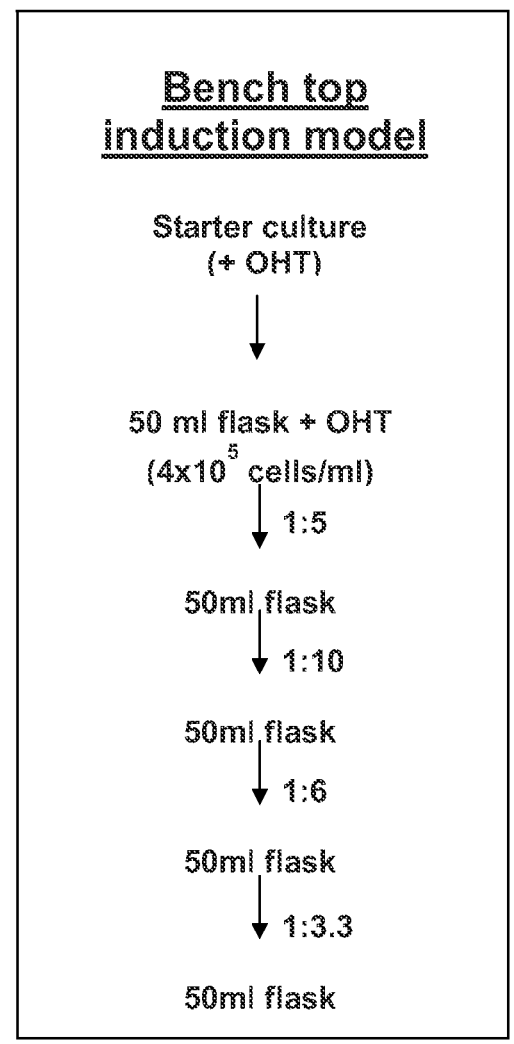
Figure 12:
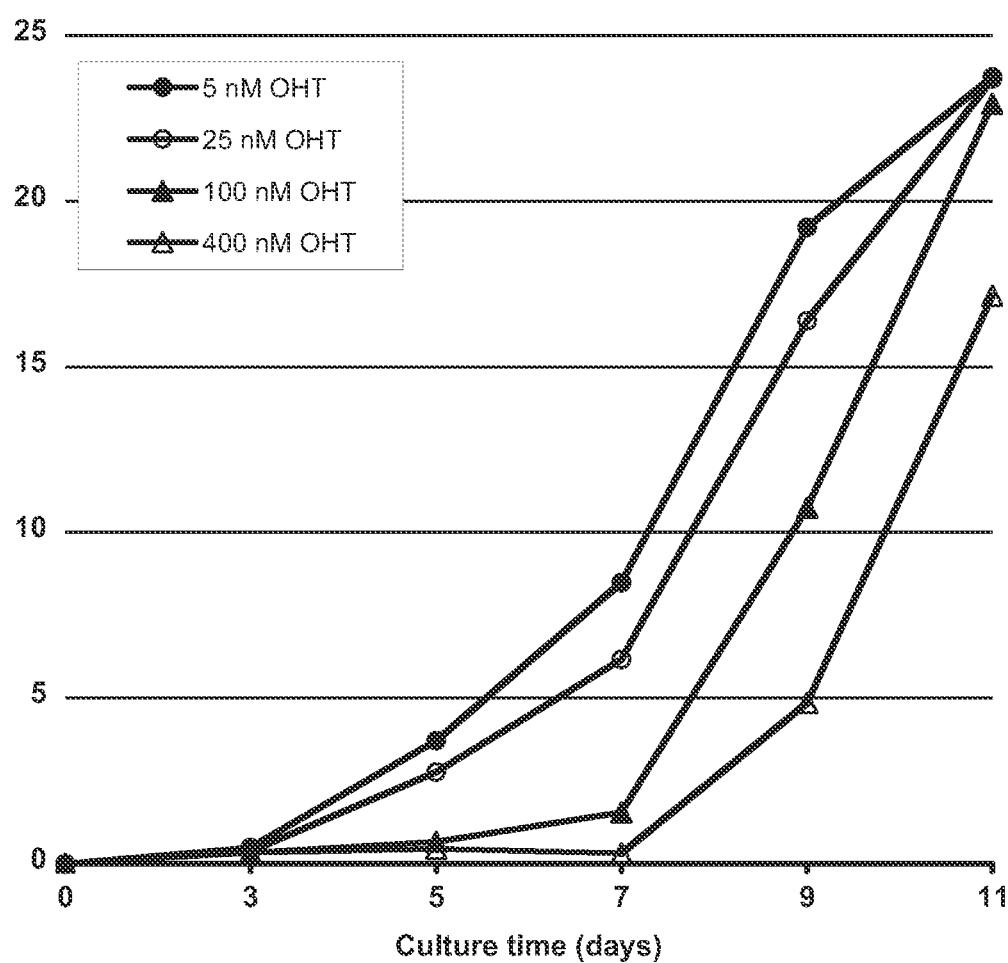
FIG. 12 shows specific productivity for protein of interest following induction, measured for various initial concentrations of OHT, for a lab bench induction model.

Removal of OHT from C110 cultures by collecting cells by centrifugation and washing away residual OHT is not practical for cells grown in bioreactors. Accordingly, we examined if induction of 13SC1132 expression in C110 cells could be achieved by dilution of OHT as a consequence of culture expansion. FIG. 11A shows a typical manufacturing seed train leading to the addition of cells to a 10,000 L bioreactor 9 days after initiating the culture. To examine the feasibility of using cell lines regulated by Arc2-ER$_{LBD}$T2 at large scale, we modeled the 10,000 L seed train at bench scale, as shown in FIG. 11B, by using the same number of dilutions of the initial starter culture. C110 cultures were grown in medium containing either 5 nM, 25 nM, 100 nM, or 400 nM OHT, then split at days 3, 5, 7, and 9, as indicated by arrows in FIG. 11B. Conditioned media were collected at each split and levels of 13SC1132 were determined by ELISA, cells were counted, and specific productivities were calculated. FIG. 12 shows that dilution of OHT from a C110 culture by seed train expansion leads to functional induction of gene expression. Furthermore, the onset of full induction may be affected by manipulating the concentration of OHT in the starter culture, and the concentration in the starter culture may be set such that full induction of expression occurs at the optimal time in the terminal bioreactor.

Example 10

Induction of 13SC1132 Expression in Batch-Fed Bioreactors

The high level expression of a secreted recombinant protein may have deleterious effects on the growth of the cell, affecting both the growth rate and the maximum cell density achieved by the culture. Accordingly, regulating the expression of a secreted recombinant protein allows induction to occur at a cell density that maximizes protein production. To determine the impact of induction time on protein production in bioreactors, we grew starter cultures of clone C110 in the absence of OHT for different times prior to inoculating bioreactors.

Cells were collected by centrifugation, washed in bioreactor medium without OHT, and seeded in 250 ml at about $0.6 \times 10^6$ cells/ml and expanded in bioreactor medium without OHT. Cultures were either split again, or fresh medium added in order to pre-induce starter cultures for 2, 4 or 6 days prior to inoculating the bioreactor. A starter culture was induced upon addition to the bioreactor (day 0 induction), and 200 nM OHT was added to the bioreactor as a control. Two liter bioreactors were seeded at $0.8 \times 10^6$ cells/ml, and maintained at 37° C., 30% dO2, pH 7.2, and were fed at 3 and 6 days after inoculation. Media was removed every day from the bioreactor and assayed for 13SC1132 expression by ELISA, and cell density was determined.

Figure 13:
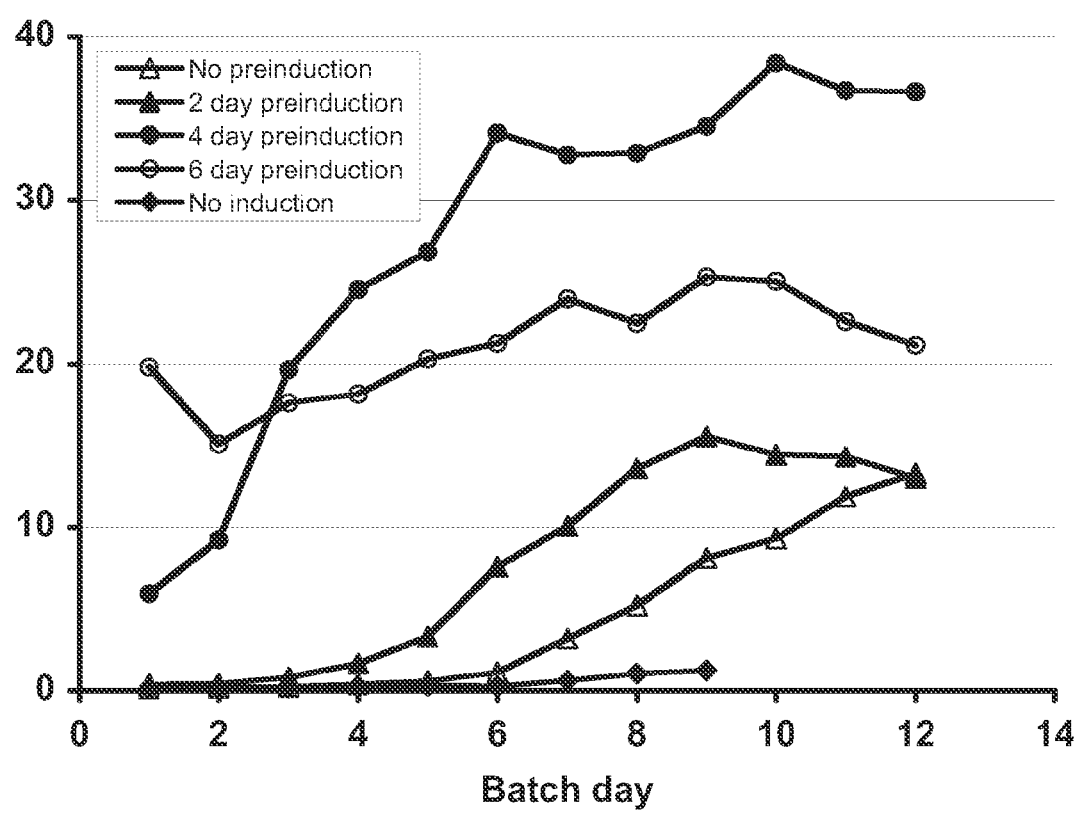
FIG. 13 shows cumulative specific productivity for a protein of interest with batch days, for pre-inductions of zero to six days, for a lab bench induction model.
Figure 14:
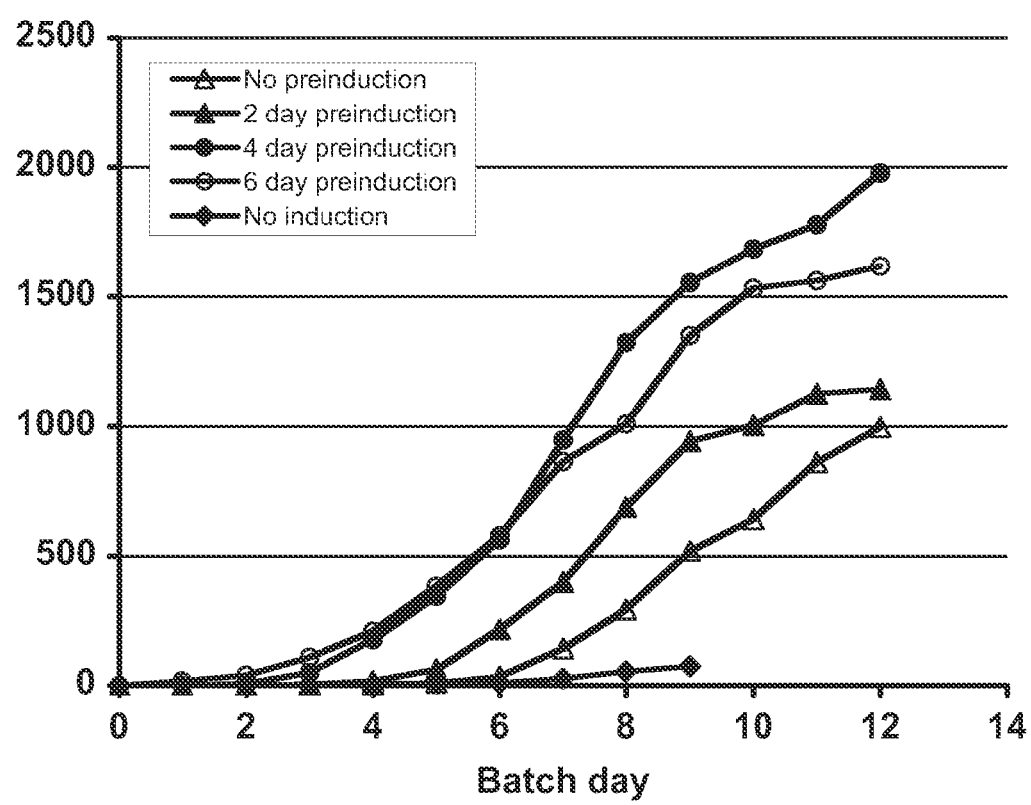
FIG. 14 shows titer as a function of batch day for pre-inductions of zero to six days, for a lab bench induction model.

FIG. 13 shows the cumulative specific productivity of bioreactor cultures started with cell cultures induced for different times prior to inoculation. Removal of OHT 4 days prior to starting the bioreactor results in the maximum specific productivity and highest production level (FIG. 14). Induction for more time (6 days) or less time (2 days) resulted in lower cumulative specific productivity and lower protein production.

We claim:

1. A method for expressing a protein of interest from a gene of interest in eukaryotic cells in a bioreactor, comprising:
   (a) seeding a starter culture for a bioreactor with eukaryotic cells in the presence of a concentration of a ligand that stabilizes a regulatory fusion protein (RFP) and inhibits expression of a protein of interest, wherein the eukaryotic cells comprise
   i. a promoter operably linked to the gene of interest encoding the protein of interest and controlled by a Tet or Arc operator operably linked and positioned 5' with respect to the promoter, and, ii. a gene encoding the regulatory fusion protein (RFP), wherein the RFP consists essentially of
   (1) a transcription blocking domain comprising (i) a TetR repressor or (ii) an Arc repressor DNA-binding domain; and
   (2) a ligand-binding domain of an estrogen receptor of SEQ ID NO:8,
   wherein the RFP inhibits expression of the gene of interest by binding to the Tet or Arc operator and inhibiting transcription in the presence of the ligand, but not in the absence of the ligand;
   wherein the ligand is capable of binding to the ligand-binding domain of an estrogen receptor;
(b) growing the cells in the starter culture to establish a culture, wherein expression of the protein of interest is inhibited;
(c) seeding a 10 liter bioreactor with the culture, wherein media employed in the 10 liter bioreactor comprises an inhibitory amount of the ligand;
(d) conducting a seed train to seed a 3,000 liter or 10,000 liter bioreactor, wherein media added subsequent to the 10 liter bioreactor does not contain the ligand, and wherein the seed train is conducted so that sufficient media is added to reduce the concentration of the ligand at the 3,000 liter or 10,000 liter stage; and
(e) growing the cells of the 3,000 liter or 10,000 liter bioreactor under conditions sufficient to express the protein of interest.

2. The method according to claim 1, wherein the protein of interest is an antibody.

3. The method according to claim 1, wherein the estrogen receptor ligand-binding domain comprises the amino acid sequence from N304 to V595 of SEQ ID NO:8.

4. The method according to claim 1, wherein the estrogen receptor ligand-binding domain has amino acid modifications valine at residue 400, alanine at residue 543, and alanine at residue 544 of the estrogen receptor (SEQ ID NO:8).

5. The method according to claim 1, wherein the ligand is selected from the group consisting of estrogen, tamoxifen, and 4-hydroxytamoxifen (OHT).

6. The method according to claim 1, wherein the TetR repressor comprises amino acids M1 to S207 of SEQ ID NO:7.

7. The method according to claim 1, wherein the Arc repressor is an Arc repressor dimer.

8. The method according to claim 7, wherein the Arc repressor dimer comprises Arc monomers connected by a linker.

9. The method of claim 1, wherein the promoter operably linked to the nucleotide sequence of interest is derived from CMV, SV40, Rous sarcoma virus, metallothionein, nopaline synthetase, cauliflower mosaic virus 35S RNA, ribulose biphosphate carboxylase, Gal4, alcohol dehydrogenase, phosphoglycerol kinase, alkaline phosphatase, elastase I, insulin, immunoglobulin, mouse mammary tumor virus, albumin, α-fetoprotein, α1-antitrypsin, β-globin, or myosin light chain-2.

10. The method of claim 9, wherein the promoter is CMV-MIE.

11. The method of claim 1, wherein the eukaryotic cell is selected from the group consisting of a COS, CHO, 293, BHK or NSO cell.

12. The method of claim 1, wherein the operator is TetO or ArcO.

13. The method of claim 1, wherein the operator is placed immediately downstream of the promoter.

14. The method of claim 1, wherein the operator is placed within 10 base pairs of the promoter.

15. The method according to claim 1, wherein the bioreactor has a capacity of 10 liters to 10,000 liters.

16. The method according to claim 15, wherein the bioreactor has a capacity of 10 liters to 3,000 liters.

17. The method according to claim 1, wherein the cells are grown in a seed train for a bioreactor, wherein the seed train comprises a 10 liter stage, a 50 liter stage, a 500 liter stage, a 3,000 liter stage, and a 10,000 liter stage, and the concentration of ligand is reduced at each stage following the 10 liter stage, such that the reduced concentration of ligand at the 10,000 liter stage is sufficient to express the protein of interest.

18. The method according to claim 17, wherein the concentration of ligand is reduced at each stage following the 10 liter stage, such that the reduced concentration of ligand at the 3,000 liter stage is sufficient to express the protein of interest.

19. The method of claim 17, wherein the concentration of ligand is reduced by adding media that does not contain any ligand that binds to the ligand-binding domain of an estrogen receptor.

20. The method of claim 17, wherein the concentration of ligand is reduced by media exchange for media that does not contain any ligand that binds to the ligand-binding domain of an estrogen receptor.

* * * * *

SEQUENCE LISTING

```
<160> NUMBER OF SEQ ID NOS: 10

<210> SEQ ID NO 1
<211> LENGTH: 11
<212> TYPE: PRT
<213> ORGANISM: Artificial Sequence
<220> FEATURE:
<223> OTHER INFORMATION: Synthetic

<400> SEQUENCE: 1

Ala Tyr Ser Gly Ser Arg Glu Leu Ile Arg Leu
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

Gly Gly Gly Ser Gly Gly Gly Thr Gly Gly Gly Ser Gly Gly Gly
1               5                   10                  15

<210> SEQ ID NO 3
<211> LENGTH: 446
<212> TYPE: PRT
<213> ORGANISM: Artificial Sequence
<220> FEATURE:
<223> OTHER INFORMATION: Synthetic

<400> SEQUENCE: 3

Met Lys Gly Met Ser Lys Met Pro Gln Phe Asn Leu Arg Trp Pro Arg
1               5                   10                  15

Glu Val Leu Asp Leu Val Arg Lys Val Ala Glu Glu Asn Gly Arg Ser
                20                  25                  30

Val Asn Ser Glu Ile Tyr Gln Arg Val Met Glu Ser Phe Lys Lys Glu
            35                  40                  45
```

-continued

```
Gly Arg Ile Gly Ala Gly Gly Ser Gly Gly Thr Gly Gly Gly
    50                  55                  60
Ser Gly Gly Gly Met Lys Gly Met Ser Lys Met Pro Gln Phe Asn Leu
65                  70                  75                  80
Arg Trp Pro Arg Glu Val Leu Asp Leu Val Arg Lys Val Ala Glu Glu
                85                  90                  95
Asn Gly Arg Ser Val Asn Ser Glu Ile Tyr Gln Arg Val Met Glu Ser
            100                 105                 110
Phe Lys Lys Glu Gly Arg Ile Gly Ala Ala Tyr Ser Gly Ser Arg Glu
        115                 120                 125
Leu Ile Arg Leu Ser Ala Gly Asp Met Arg Ala Ala Asn Leu Trp Pro
    130                 135                 140
Ser Pro Leu Met Ile Lys Arg Ser Lys Lys Asn Ser Leu Ala Leu Ser
145                 150                 155                 160
Leu Thr Ala Asp Gln Met Val Ser Ala Leu Leu Asp Ala Glu Pro Pro
                165                 170                 175
Ile Leu Tyr Ser Glu Tyr Asp Pro Thr Arg Pro Phe Ser Glu Ala Ser
            180                 185                 190
Met Met Gly Leu Leu Thr Asn Leu Ala Asp Arg Glu Leu Val His Met
        195                 200                 205
Ile Asn Trp Ala Lys Arg Val Pro Gly Phe Val Asp Leu Thr Leu His
    210                 215                 220
Asp Gln Val His Leu Leu Glu Cys Ala Trp Leu Glu Ile Leu Met Ile
225                 230                 235                 240
Gly Leu Val Trp Arg Ser Met Glu His Pro Val Lys Leu Leu Phe Ala
                245                 250                 255
Pro Asn Leu Leu Leu Asp Arg Asn Gln Gly Lys Cys Val Glu Gly Met
            260                 265                 270
Val Glu Ile Phe Asp Met Leu Leu Ala Thr Ser Ser Arg Phe Arg Met
        275                 280                 285
Met Asn Leu Gln Gly Glu Glu Phe Val Cys Leu Lys Ser Ile Ile Leu
    290                 295                 300
Leu Asn Ser Gly Val Tyr Thr Phe Leu Ser Ser Thr Leu Lys Ser Leu
305                 310                 315                 320
Glu Glu Lys Asp His Ile His Arg Val Leu Asp Lys Ile Thr Asp Thr
                325                 330                 335
Leu Ile His Leu Met Ala Lys Ala Gly Leu Thr Leu Gln Gln Gln His
            340                 345                 350
Gln Arg Leu Ala Gln Leu Leu Leu Ile Leu Ser His Ile Arg His Met
        355                 360                 365
Ser Asn Lys Gly Met Glu His Leu Tyr Ser Met Lys Cys Lys Asn Val
    370                 375                 380
Val Pro Leu Tyr Asp Leu Leu Leu Glu Ala Ala Asp Ala His Arg Leu
385                 390                 395                 400
His Ala Pro Thr Ser Arg Gly Gly Ala Ser Val Glu Glu Thr Asp Gln
                405                 410                 415
Ser His Leu Ala Thr Ala Gly Ser Thr Ser Ser His Ser Leu Gln Lys
            420                 425                 430
Tyr Tyr Ile Thr Gly Glu Ala Glu Gly Phe Pro Ala Thr Val
        435                 440                 445

<210> SEQ ID NO 4
<211> LENGTH: 26
```

<212> TYPE: DNA
<213> ORGANISM: Artificial Sequence
<220> FEATURE:
<223> OTHER INFORMATION: Synthetic

<400> SEQUENCE: 4
gagtatttac ggtaaactgc ccactt                                          26

<210> SEQ ID NO 5
<211> LENGTH: 86
<212> TYPE: DNA
<213> ORGANISM: Artificial Sequence
<220> FEATURE:
<223> OTHER INFORMATION: Synthetic

<400> SEQUENCE: 5
gagagatctg agtcgacata gtagagtgct tctatcatga atagtagagt gcttctatca    60
tgagctctgc ttatatagac ctccca                                          86

<210> SEQ ID NO 6
<211> LENGTH: 116
<212> TYPE: DNA
<213> ORGANISM: Artificial Sequence
<220> FEATURE:
<223> OTHER INFORMATION: Synthetic

<400> SEQUENCE: 6
tataagcaga gctcatgata gaatcactct actattcatg atagaagcac tctactatat    60
attcgtctcg agtactatct tagtgagatg ataagtacta tcttcgtgag atgata       116

<210> SEQ ID NO 7
<211> LENGTH: 207
<212> TYPE: PRT
<213> ORGANISM: Filamentous phage

<400> SEQUENCE: 7

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu

```
                180                 185                 190
Ile Ile Cys Gly Leu Glu Lys Gln Leu Lys Cys Glu Ser Gly Ser
                195                 200                 205

<210> SEQ ID NO 8
<211> LENGTH: 595
<212> TYPE: PRT
<213> ORGANISM: Homo sapiens

<400> SEQUENCE: 8

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
            35                  40                  45

Pro Ala Val Tyr Asn Tyr Pro Glu Gly Ala Ala Tyr Glu Phe Asn Ala
        50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350
```

-continued

```
Glu Leu Val His Met Ile Asn Trp Ala Lys Arg Val Pro Gly Phe Val
            355                 360                 365
Asp Leu Thr Leu His Asp Gln Val His Leu Leu Glu Cys Ala Trp Leu
370                 375                 380
Glu Ile Leu Met Ile Gly Leu Val Trp Arg Ser Met Glu His Pro Gly
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
            420                 425                 430
Ser Arg Phe Arg Met Met Asn Leu Gln Gly Glu Glu Phe Val Cys Leu
        435                 440                 445
Lys Ser Ile Ile Leu Leu Asn Ser Gly Val Tyr Thr Phe Leu Ser Ser
    450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
            500                 505                 510
His Ile Arg His Met Ser Asn Lys Gly Met Glu His Leu Tyr Ser Met
        515                 520                 525
Lys Cys Lys Asn Val Val Pro Leu Tyr Asp Leu Leu Leu Glu Met Leu
    530                 535                 540
Asp Ala His Arg Leu His Ala Pro Thr Ser Arg Gly Gly Ala Ser Val
545                 550                 555                 560
Glu Glu Thr Asp Gln Ser His Leu Ala Thr Ala Gly Ser Thr Ser Ser
                565                 570                 575
His Ser Leu Gln Lys Tyr Tyr Ile Thr Gly Glu Ala Glu Gly Phe Pro
            580                 585                 590
Ala Thr Val
        595
```

```
<210> SEQ ID NO 9
<211> LENGTH: 21
<212> TYPE: DNA
<213> ORGANISM: Enterobacteria phage P22

<400> SEQUENCE: 9
atgatagaat cactctacta t                                           21

<210> SEQ ID NO 10
<211> LENGTH: 65
<212> TYPE: DNA
<213> ORGANISM: Artificial Sequence
<220> FEATURE:
<223> OTHER INFORMATION: Synthetic

<400> SEQUENCE: 10
gagagatctg agtcgacgaa tagtagagtg cttctatcat gagctctgct tatatagacc    60
tccca                                                              65
```